United States Patent
Buyse

(10) Patent No.: US 11,753,465 B2
(45) Date of Patent: Sep. 12, 2023

(54) NUCLEIC ACIDS ENCODING POLYPEPTIDES AGAINST IL-23

(71) Applicants: Ablynx N.V., Ghent-Zwijnaarde (BE); Sanofi, Paris (FR)

(72) Inventor: Marie-Ange Buyse, Merelbeke (BE)

(73) Assignees: Ablynx N.V., Zwijnaarde (BE); Sanofi, Paris (FR)

( * ) Notice: Subject to any disclaimer, the term of this patent is extended or adjusted under 35 U.S.C. 154(b) by 249 days.

(21) Appl. No.: 17/188,158

(22) Filed: Mar. 1, 2021

(65) Prior Publication Data
US 2021/0188967 A1    Jun. 24, 2021

Related U.S. Application Data

(63) Continuation of application No. 15/769,864, filed as application No. PCT/EP2016/076076 on Oct. 28, 2016, now Pat. No. 10,968,271.

(60) Provisional application No. 62/248,468, filed on Oct. 30, 2015.

(51) Int. Cl.
| | |
|---|---|
| C07K 16/24 | (2006.01) |
| A61P 35/00 | (2006.01) |
| C07K 16/42 | (2006.01) |
| A61P 31/00 | (2006.01) |

(52) U.S. Cl.
CPC ............ C07K 16/244 (2013.01); A61P 35/00 (2018.01); A61P 31/00 (2018.01); C07K 16/4208 (2013.01); C07K 2317/22 (2013.01); C07K 2317/34 (2013.01); C07K 2317/56 (2013.01); C07K 2317/569 (2013.01)

(58) Field of Classification Search
None
See application file for complete search history.

(56) References Cited

U.S. PATENT DOCUMENTS

| | | | |
|---|---|---|---|
| 5,595,756 A | 1/1997 | Bally et al. | |
| 10,968,271 B2 | 4/2021 | Buyse | |

FOREIGN PATENT DOCUMENTS

| | | | |
|---|---|---|---|
| EA | 201000424 A1 | 10/2010 | |
| JP | 2011-504740 A | 2/2011 | |
| JP | 2013-515460 A | 5/2013 | |
| JP | 2013-525408 A | 6/2013 | |
| JP | 2014-520134 A | 8/2014 | |
| JP | 2014-525752 A | 10/2014 | |
| WO | WO 2009/068627 A2 | 6/2009 | |
| WO | WO-2009068627 A2 * | 6/2009 | ......... A61K 39/3955 |
| WO | WO 2010/125187 A2 | 11/2010 | |
| WO | WO 2010/142534 A1 | 12/2010 | |
| WO | WO 2011/075861 A1 | 6/2011 | |
| WO | WO 2011/135026 A1 | 11/2011 | |
| WO | WO 2012/175471 A1 | 12/2012 | |
| WO | WO 2014/111550 A1 | 7/2014 | |
| WO | WO 2017/085172 A2 | 5/2017 | |

OTHER PUBLICATIONS

[No Author Listed], ICD-10 Version: 2016. 1 page.
Auerbach et al., Angiogenesis assays: problems and pitfalls. Cancer Metastasis Rev. 2000;19(1-2):167-72. doi: 10.1023/a:1026574416001.
Blumberg et al., Unraveling the autoimmune translational research process layer by layer. Nat Med. Jan. 6, 2012;18(1):35-41. doi: 10.1038/nm.2632.
Chen et al., Anti-IL-23 therapy inhibits multiple inflammatory pathways and ameliorates autoimmune encephalomyelitis. J Clin Invest. May 2006;116(5):1317-26. doi: 10.1172/JCI25308.
Cocco et al., Interleukin-23 acts as antitumor agent on childhood B-acute lymphoblastic leukemia cells. Blood. Nov. 11, 2010;116(19):3887-98. doi: 10.1182/blood-2009-10-248245. Epub Jul. 29, 2010.
Croxford et al., IL-23: one cytokine in control of autoimmunity. Eur J Immunol. Sep. 2012;42(9):2263-73. doi: 10.1002/eji.201242598.
Gura, Systems for identifying new drugs are often faulty. Science. Nov. 7, 1997;278(5340):1041-2. doi: 10.1126/science.278.5340.1041.
Hogenesch et al., Challenges in pre-clinical testing of anti-cancer drugs in cell culture and in animal models. J Control Release. Dec. 10, 2012;164(2):183-6. doi: 10.1016/j.jconrel.2012.02.031. Epub Mar. 14, 2012.
Jain, Barriers to drug delivery in solid tumors. Sci Am. Jul. 1994;271(1):58-65. doi: 10.1038/scientificamerican0794-58.
Li et al., Mechanisms of pathogenesis in allergic asthma: role of interleukin-23. Respirology. Jul. 2014;19(5):663-9. doi: 10.1111/resp.12299. Epub Apr. 30, 2014.
Longbrake et al., Why did IL-12/IL-23 antibody therapy fail in multiple sclerosis? Expert Rev Neurother. Mar. 2009;9(3):319-21. doi: 10.1586/14737175.9.3.319.
Ma, Animal Models of Disease. Modern Drug Discovery. Jun. 2004:30-36.
Mirlekar et al., IL-12 Family Cytokines in Cancer and Immunotherapy. Cancers (Basel). Jan. 6, 2021;13(2):167. doi: 10.3390/cancers13020167.
Pastor-Fernández et al., Decoding IL-23 Signaling Cascade for New Therapeutic Opportunities. Cells. Sep. 7, 2020;9(9):2044. doi: 10.3390/cells9092044.
Rudikoff et al., Single amino acid substitution altering antigen-binding specificity. Proc Natl Acad Sci USA. Mar. 1982;79(6):1979-83. doi: 10.1073/pnas.79.6.1979.

(Continued)

*Primary Examiner* — Brian Gangle
*Assistant Examiner* — Andrea K McCollum
(74) *Attorney, Agent, or Firm* — Wolf, Greenfield & Sacks, P.C.

(57) ABSTRACT

The present invention relates to amino acid sequences that are directed against interleukin 23 (IL-23). The amino acid sequences of the present invention comprise two NANOBODY® molecules against IL-23 and one NANOBODY® molecule against serum albumin, linked by two linkers. In particular, the invention relates to the amino acid sequences of SEQ ID NO: 2 and SEQ ID NO: 3 (listed in Table 1 and FIG. 1) (also referred to herein as "anti-IL 23 polypeptides of the invention").

12 Claims, 13 Drawing Sheets

Specification includes a Sequence Listing.

(56) References Cited

OTHER PUBLICATIONS

Safdari et al., Antibody humanization methods—a review and update. Biotechnol Genet Eng Rev. 2013;29:175-86. doi: 10.1080/02648725.2013.801235. Epub Aug. 2, 2013.

Soeen et al., Guselkumab (an IL-23-specific mAb) demonstrates clinical and molecular response in patients with moderate-to-severe psoriasis. J Allergy Clin Immunol. Apr. 2014; 133(4):1032-40. doi: 10.1016/j.jaci.2014.01.025.

Sporn et al., Chemoprevention of cancer. Carcinogenesis. Mar. 2000;21(3):525-30. doi: 10.1093/carcin/21.3.525.

Steinman et al., Optimization of current and future therapy for autoimmune diseases. Nat Med. Jan. 6, 2012;18(1):59-65. doi: 10.1038/nm.2625.

Tang et al., Interleukin-23: as a drug target for autoimmune inflammatory diseases. Immunology. Feb. 2012;135(2):112-24. doi: 10.1111/j.1365-2567.2011.03522.x.

Tuskey et al., Profile of ustekinumab and its potential in patients with moderate-to-severe Crohn's disease. Clin Exp Gastroenterol. May 23, 2014;7:173-9. doi: 10.2147/CEG.S39518.

Yannam et al., IL-23 in infections, inflammation, autoimmunity and cancer: possible role in HIV-1 and AIDS. J Neuroimmune Pharmacol. Mar. 2012;7(1):95-112. doi: 10.1007/s11481-011-9315-2. Epub Sep. 24, 2011.

\* cited by examiner

Figure 1

| # | Source | Sequence |
|---|---|---|
| 1 | Reference sequence | DVQLLESGGGLVQPGGSLRLSCAASGRIFSLPASGNIFNLLTIAWYRQAPGKGRELVATINSGRTYYADSVKGRFTISRDNSKNTVYLQMNSLRPEDTAVYYCQTSGSGSPNFWGQGTLVTVSSGGGSEVQLVESGGGLVQPGNSLRLSCAASGFTFSSFQMSWVRQAPGKGLEWVSSISGSGSDTLYADSVKGRFTISRDNAKTTLYLQMNSLRPEDTAVYYCTIGGSLSRSSQGTLVTVSSGGGGSEVQLLESGGVVQPGGSLRLSCAASGRTLSSYAMGWFRQAPGKGREFVARISQGGTAIYYADSVKGRFTISRDNSKNTLYLQMNSLRPEDTALYYCAKDPSPYYRGSAYLLSGSYDSWGQGTLVTVSS |
| 2 | Invention | DVQLLESGGGVVQPGGSLRLSCAASGRIFSLPASGNIFNLLTIAWYRQAPGKGRELVATINSGRTYYADSVKGRFTISRDNSKKTVYLQMNSLRPEDTALYYCQTSGSGSPNFWGQGTLVTVSSGGGGSGGGSEVQLVESGGGVVQPGNSLRLSCAASGFTFSSFQMSWVRQAPGKGLEWVSSISGSGSDTLYADSVKGRFTISRDNAKTTLYLQMNSLRPEDTALYYCTIGGSLSRSSQGTLVTVSSGGGGSEVQLLESGGVVQPGGSLRLSCAASGRTLSSYAMGWFRQAPGKGREFVARISQGGTAIYYADSVKGRFTISRDNSKNTLYLQMNSLRPEDTALYYCAKDPSPYYRGSAYLLSGSYDSWGQGTLVTVSSA |
| 3 | Invention | DVQLLESGGGVVQPGGSLRLSCAASGRIFSLPASGNIFNLLTIAWYRQAPGKGRELVATINSGRTYYADSVKGRFTISRDNSKKTVYLQMNSLRPEDTALYYCQTSGSGSPNFWGQGTLVKVSSGGGGSGGGSEVQLVESGGGVVQPGNSLRLSCAASGFTFSSFQMSWVRQAPGKGLEWVSSISGSGSDTLYADSVKGRFTISRDNAKTTLYLQMNSLRPEDTALYYCTIGGSLSRSSQGTLVKVSSGGGGSEVQLLESGGVVQPGGSLRLSCAASGRTLSSYAMGWFRQAPGKGREFVARISQGGTAIYYADSVKGRFTISRDNSKNTLYLQMNSLRPEDTALYYCAKDPSPYYRGSAYLLSGSYDSWGQGTLVKVSSA |
| 4 | WO 2009/068627; SEQ ID NO:2537 | EVQLVESGGGLVQAGGSLRLSCAASGRIFSLPASGNIFNLLTIAWHRQAPGMQRELVATINSGSRTNYADSVKGRFTISRDNAQKTVYLQMNNLKPEDTAVYYCQTSGSGSPNFWGQGTQVTVSSGGGGSGGGSEVQLVESGGGSEVQLVESGGGGSGGGSEVQLVESGGGGSGGGSEVQLVESGGGGSGGGSEVQLVESGGGSEVQLVESGGGSEVQLVESGGGSEVQLVESGGGSEVQLVESGGGLVQPGGSLRLSCIASGLPFSTKSMGWFRQAPGKEREFVARISPGGTSRYYGDFVKGRFAISRDNAKNTTWLQMNSLKAEDTAVYYCASGERSTYIGSNYYRTNEYDYWGTGTQVTVSS |
| 5 | WO 2009/068627; SEQ ID NO:2543 | EVQLVESGGGLVQAGGSLRLSCAASGRIFSLPASGNIFNLLTIAWYRQAPGMQRELVATINSGSRTNYADSVKGRFTISRDNAQKTVYLQMNNLKPEDTAVYYCQTSGSGSPNFWGQGTQVTVSSGGGGSGGGSEVQLVESGGGLVQPGNSLRLSCAASGFTFRSFQMSWVRQAPGKEPEWVSSISGSGSDTLYADSVKGRFTISRDNAKTTLYLQMNSLKPEDTAVYYCTIGGSLSRSSQGTQVTVSSGGGGSGGGSEVQLVESGGGLVQPGGSLRLSCAASGRTLSSYAMGWFRQAPGKEREFVARISQGGTAIYYADSVKGRFTISRDNAKNTVYLQMNSLKPEDTAVYYCAKDPSPYYRGSAYLLSGSRTNYADSVKGRFTISRDNAKNTVYLQMNSLKPEDTAVYYCAKDPSPYY |

Figure 1 (continued)

| | | |
|---|---|---|
| 6 | WO 2009/068627; SEQ ID NO:2544 | EVQLVESGGGLVQAGGSLRLSCAASGRIFSLPASGNIFNLLTIAWYRQAPGKQRELVATINSGSRTNYADSVKG RFTISRDNAQKTVYLQMNNLKPEDTAVYYCQTSGSGSPNFWGQGTQVTVSSGGGGSGGGGSEVQLVESGGGL VQPGNSLRLSCAASGFTFRSFGMSWVRQAPGKEPEWVSSISGSDTLYADSVKGRFTISRDNAKTTLYLQMN SLKPEDTAVYYCTIGGSLSRSSQGTQVTVSSGGGGSGGGGSEVQLVESGGGLVQAGGSLRLSCAASGRTLSSYA MGWFRQAPGKEREFVARISQGTAIYYADSVKGRFTISRDNAKNTVYLQMNSLKPEDTAVYYCAKDPSPYYR GSAYLLSGSYDSWGQGTQVTVSS |
| 7 | WO 2009/068627; SEQ ID NO:2546 | EVQLVESGGGLVQAGGSLRLSCAASGRIFSLPASGNIFNLLTIAWHRQAPGMQRELVATINSGSRTNYADSVK GRFTISRDNAKTVYLQMNNLKPEDTAVYYCQTSGSGSPNFWGQGTQVTVSSGGGGSGGGGSEVQLVESGGG LVQPGNSLRLSCAASGFTFRSFQMSWVRQAPGKEPEWVSSISGSGSDTLYADSVKGRFTISRDNAKTTLYLQM NSLKPEDTAVYYCTIGGSLSRSSQGTQVTVSSGGGGSGGGGSEVQLVESGGGLVQAGGSLRLSCAASGRTLSSY AMGWFRQAPGKEREFVARISQGTAIYYADSVKGRFTISRDNAKNTVYLQMNSLKPEDTAVYYCAKDPSPYY RGSAYLLSGSYDSWGQGTQVTVSS |
| 8 | WO 2009/068627; SEQ ID NO:2547 | EVQLVESGGGLVQAGGSLRLSCAASGRIFSLPASGNIFNLLTIAWHRQAPGMQRELVATINSGSRTNYADSVK GRFTISRDNAKTVYLQMNNLKPEDTAVYYCQTSGSGSPNFWGQGTQVTVSSGGGGSGGGGSEVQLVESGGG LVQPGNSLRLSCAASGFTFRSFGMSWVRQAPGKEPEWVSSISGSGSDTLYADSVKGRFTISRDNAKTTLYLQM NSLKPEDTAVYYCTIGGSLSRSSQGTQVTVSSGGGGSGGGGSEVQLVESGGGLVQAGGSLRLSCAASGRTLSSY AMGWFRQAPGKEREFVARISQGTAIYYADSVKGRFTISRDNAKNTVYLQMNSLKPEDTAVYYCAKDPSPYY RGSAYLLSGSYDSWGQGTQVTVSS |
| 9 | WO 2009/068627; SEQ ID NO:2615 | EVQLLESGGGLVQPGGSLRLSCAASGRIFSLPASGNIFNLLTIAWYRQAPGKGRELVATINSGSRTNYADSVKG RFTISRDNSKNTLYLQMNSLRPEDTAVYYCQTSGSGSPNFWGQGTLVTVSSGGGGSGGGGSEVQLVESGGGLV QPGNSLRLSCAASGFTFSSFGMSWVRQAPGKGLEWVSSISGSGSDTLYADSVKGRFTISRDNAKTTLYLQMNS LRPEDTAVYYCTIGGSLSRSSQGTLVTVSSGGGGSGGGGSEVQLLESGGGLVQPGGSLRLSCAASGRTLSSYAM GWFRQAPGKGREFVSRISQGGTAIYYADSVKGRFTISRDNSKNTLYLQMNSLRPEDTAVYYCAKDPSPYYRGS AYLLSGSYDSWGQGTLVTVSS |
| 10 | WO 2009/068627; SEQ ID NO:2616 | EVQLLESGGGLVQPGGSLRLSCAASGRIFSLPASGNIFNLLTIAWYRQAPGKGRELVATINSGSRTYYADSVKG RFTISRDNSKKTLYLQMNSLRPEDTAVYYCQTSGSGSPNFWGQGTLVTVSSGGGGSGGGGSEVQLVESGGGLV QPGNSLRLSCAASGFTFSSFGMSWVRQAPGKGLEWVSSISGSGSDTLYADSVKGRFTISRDNAKTTLYLQMNS LRPEDTAVYYCTIGGSLSRSSQGTLVTVSSGGGGSCGGGSEVQLLESGGGLVQPGGSLRLSCAASGRTLSSYAM GWFRQAPGKGREFVSRISQGGTAIYYADSVKGRFTISRDNSKNTLYLQMNSLRPEDTAVYYCAKDPSPYYRGS AYLLSGSYDSWGQGTLVTVSS |

Figure 1 (continued)

| | | |
|---|---|---|
| 11 | WO 2009/068627; SEQ ID NO:2617 | EVQLLESGGGLVQPGGSLRLSCAASGFTFRSFGMSWVRQAPGKEPEWVSSISGSGGSTYYADSVKGRFTISRDNSKNTLYLQMNSLRPEDTAVYYCTIGGSLSRSSQGTVTVSSGGGGSGGGGSGGGGSEVQLLESGGGLVQPGGSLRLSCAASGRTLSSYAMGWFRQAPGKGREFVSRISQGGTAIYYADSVKGRFTISRDNSKNTLYLQMNSLRPEDTAVYYCAKDPSPYYRGSAYLLSGSYDSWGQGTLVTVSS |
| 12 | WO 2009/068627; SEQ ID NO:2618 | EVQLLESGGGLVQPGGSLRLSCAASGFTFRSFGMSWVRQAPGKGRELVATINSGSRTYYADSVKGRFTISRDNSKKTLYLQMNSLRPEDTAVYYCTIGGSLSRSSQGTVTVSSGGGGSGGGGSGGGGSEVQLVESGGGLVQPGNSLRLSCAASGFTFRSFGMSWVRQAPGKEPEWVSSISGSGGSTYYADSVKGRFTISRDNAKTTLYLQMNSLRPEDTAVYYCTIGGSLSRSSQGTVTVSSGGGGSGGGGSGGGGSEVQLLESGGGLVQPGGSLRLSCAASGRTLSSYAMGWFRQAPGKGREFVSRISQGGTAIYYADSVKGRFTISRDNSKNTLYLQMNSLRPEDTAVYYCAKDPSPYYRGSAYLLSGSYDSWGQGTLVTVSS |
| 13 | WO 2009/068627; SEQ ID NO:2622 | EVQLLESGGGLVQPGGSLRLSCAASGRIFSLPASGNIFNLLTIAWYRQAPGKGRELVATINSGSRTYYADSVKGRFTISRDNSKKTLYLQMNSLRPEDTAVYYCQTSGSGSPNFWGQGTLVTVSSGGGGSGGGGSGGGGSEVQLVESGGGLVQPGNSLRLSCAASGFTFSSFGMSWVRQAPGKGLEWVSSISGSGGSTYYADSVKGRFTISRDNAKTTLYLQMNSLRPEDTAVYYCTIGGSLSRSSQGTLVTVSSGGGGSGGGGSGGGGSEVQLLESGGGLVQPGGSLRLSCAASGRTLSSYAMGWFRQAPGKGREFVARISQGGTAIYYADSVKGRFTISRDNSKNTLYLQMNSLRPEDTAVYYCAKDPSPYYRGSAYLLSGSYDSWGQGTLVTVSS |
| 14 | WO 2010/142534; SEQ ID NO:16 | EVQLLESGGGLVQPGGSLRLSCAASGRIFSLPASGNIFNLLTIAWYRQAPGKGRELVATINSGSRTYYADSVKGRFTISRDNSKKTVYLQMNSLRPEDTAVYYCQTSGSGSPNFWGQGTLVTVSSGGGGSGGGGSGGGGSEVQLVESGGGLVQPGNSLRLSCAASGFTFSSFGMSWVRQAPGKGLEWVSSISGSGGSTYYADSVKGRFTISRDNAKTTLYLQMNSLRPEDTAVYYCTIGGSLSRSSQGTLVTVSSGGGGSGGGGSGGGGSEVQLLESGGGLVQPGGSLRLSCAASGRTLSSYAMGWFRQAPGKGRELVATINSGSRTYYADSVKGRFTISRDNAKTTLYLQMNSLRPEDTAVYYCAKDPSPYYRGSAYLLSGSYDSWGQGTLVTVSS |
| 15 | WO 2010/142534; SEQ ID NO:17 | EVQLLESGGGLVQPGGSLRLSCAASGRIFSLPASGNIFNLLTIAWYRQAPGKGRELVATINSGSRTYYADSVKGRFTISRDNSKKTVYLQMNSLRPEDTAVYYCQTSGSGSPNFWGQGTLVTVSSGGGGSGGGGSGGGGSEVQLVESGGGLVQPGNSLRLSCAASGFTFSSFGMSWVRQAPGKEPEWVSSISGSGGSTYYADSVKGRFTISRDNAKTTLYLQMNSLRPEDTAVYYCTIGGSLSRSSQGTVTVSSGGGGSGGGGSGGGGSEVQLLESGGGLVQPGGSLRLSCAASGRTLSSYAMGWFRQAPGKGRELVATINSGSRTYYADSVKGRFTISRDNAKTTLYLQMNSLRPEDTAVYYCAKDPSPYYRGSAYLLSGSYDSWGQGTLVTVSS |

Figure 1 (continued)

| | | |
|---|---|---|
| 16 | WO 2010/142534;<br>SEQ ID NO:18 | EVQLLESGGGLVQPGGSLRLSCAASGRIFSLPASGNIFNLLTIAWYRQAPGKGRELVATINSGSRTYYADSVKG<br>RFTISRDNSKKTVYLQMNSLRPEDTAVYYCAASGRTLSSYAM<br>QPGNSLRLSCAASGFTFSSFQMSWVRQAPGKGLEWVSSISGSGSDTLYADSVKGRFTISRDNAKTTLYLQMNS<br>LRPEDTAVYYCTIGGSLSRSSQGTLVTVSSGGGGSGGGGSEVQLLESGGGLVQPGGSLRLSCAASGRTLSSYAM<br>GWFRQAPGKGREFVARISQGGTAIYYADSVKGRFTISRDNSKNTVYLQMNSLRPEDTAVYYCAKDPSPYYRG<br>SAYLLSGSYDSWGQGTLVTVSS |
| 17 | WO 2010/142534;<br>SEQ ID NO:19 | EVQLLESGGGLVQPGGSLRLSCAASGRIFSLPASGNIFNLLTIAWYRQAPGKGRELVATINSGSRTYYADSVKG<br>RFTISRDNSKKTVYLQMNSLRPEDTAVYYCQTSGSGSPNFWGQGTLVTVSSGGGGSGGGGSEVQLVESGGGLV<br>QPGNSLRLSCAASGFTFRSFGMSWVRQAPGKEPEWVSSISGSGSDTLYADSVKGRFTISRDNAKTTLYLQMNS<br>LKPEDTAVYYCTIGGSLSRSSQGTQVTVSSGGGGSGGGGSEVQLVESGGGLVQAGGSLRLSCAASGRTLSSYAM<br>GWFRQAPGKEREFVARISQGGTAIYYADSVKGRFTISRDNAKNTVYLQMNSLRPEDTAVYYCAKDPSPYYRG<br>SAYLLSGSYDSWGQGTQVTVSS |
| 18 | WO 2010/142534;<br>SEQ ID NO:23 | EVQLLESGGGLVQPGGSLRLSCAASGRIFSLPASGNIFNLLTIAWYRQAPGKGRELVATINSGSRTYYADSVKG<br>RFTISRDNSKKTVYLQMNSLRPEDTAVYYCQTSGSGSPNFWGQGTLVTVSSGGGGSGGGGSEVQLVESGGGLV<br>QPGNSLRLSCAASGFTFSSFGMSWVRQAPGKGLEWVSSISGSGSDTLYADSVKGRFTISRDNAKTTLYLQMNS<br>LRPEDTAVYYCTIGGSLSRSSQGTLVTVSSGGGGSGGGGSEVQLLESGGGLVQPGGSLRLSCAASGRTLSSYAM<br>GWFRQAPGKGREFVARISQGGTAIYYADSVKGRFTISRDNSKNTLYLQMNSLRPEDTAVYYCAKDPSPYYRG<br>SAYLLSGSYDSWGQGTLVTVSS |
| 19 | WO 2010/142534;<br>SEQ ID NO:24 | EVQLLESGGGLVQPGGSLRLSCAASGRIFSLPASGNIFNLLTIAWYRQAPGKGRELVATINSGSRTYYADSVKG<br>RFTISRDNSKKTVYLQMNSLRPEDTAVYYCQTSGSGSPNFWGQGTLVTVSSGGGGSGGGGSEVQLVESGGGLV<br>QPGNSLRLSCAASGFTFSSFGMSWVRQAPGKGLEWVSSISGSGSDTLYADSVKGRFTISRDNAKTTLYLQMNS<br>LRPEDTAVYYCTIGGSLSRSSQGTLVTVSSGGGGSGGGGSEVQLLESGGGLVQPGGSLRLSCAASGRTLSSYAM<br>GWFRQAPGKGREFVARISQGGTAIYYADSVKGRFTISRDNSKNTVYLQMNSLRPEDTAVYYCAKDPSPYYRG<br>SAYLLSGSYDSWGQGTLVTVSS |
| 20 | WO2011/135026;<br>SEQ ID NO:8 | EVQLLESGGGLVQPGGSLRLSCAASGRIFSLPASGNIFNLLTIAWYRQAPGKGRELVATINSGSRTYYADSVKG<br>RFTISRDNSKKTVYLQMNSLRPEDTAVYYCQTSGSGSPNFWGQGTLVTVSSGGGGSGGGGSEVQLVESGGGLV<br>QPGNSLRLSCAASGFTFSSFGMSWVRQAPGKGLEWVSSISGSGSDTLYADSVKGRFTISRDNAKTTLYLQMNS<br>LRPEDTAVYYCTIGGSLSRSRISQGGTAIYYADSVKGRFTISRDNSKNTLYLQMNSLRPEDTAVYYCAKDPSPYYRGS<br>GWFRQAPGKGREFVSRISQGGTAIYYADSVKGRFTISRDNSKNTLYLQMNSLRPEDTAVYYCAKDPSPYYRGS<br>AYLLSGSYDSWGQGTLVTVSS |

Figure 1 (continued)

| 21 | WO2011/135026: SEQ ID NO:12 | EVQLLESGGGLVQPGGSLRLSCAASGRIFSLPASGNIFNLLTIAWYRQAPGKGRELVATINSGSRTYYADSVKGRFTISRDNSKKTVYLQMNSLRPEDTAVYYCAASGFTFSSFQMSWVRQAPGKGLEWVSSISGSGSDTLYADSVKGRFTISRDNAKTTLYLQMNSLRPEDTAVYYCTIGGSLSRSSQGTLVTVSSGGGGSGGGGSEVQLLESGGGLVQPGGSLRLSCAASGRTLSSYAMGWFRQAPGKGREFVARISQGGTAIYYADSVKGGTAIYYADSVKGRFTISRDNSKNTLYLQMNSLRPEDTAVYYCAKDPSPYYRGSAYLLSGSYDSWGQGTLVTVSS |
| 22 | WO2011/135026: SEQ ID NO:36 | EVQLLESGGGLVQPGGSLRLSCAASGRIFSLPASGNIFNLLTIAWYRQAPGKGRELVATINSGSRTYYADSVKGRFTISRDNSKKTVYLQMNSLRPEDTAVYYCAASGFTFSSFQMSWVRQAPGKGLEWVSSISGSGSDTLYADSVKGRFTISRDNAKTTLYLQMNSLRPEDTAVYYCTIGGSLSRSSQGTLVTVSSGGGGSGGGGSEVQLLESGGGLVQPGGSLRLSCAASGRTLSSYAMGWFRQAPGKGREFVARISQGGTAIYYADSVKGRFTISRDNSKNTLYLQMNSLRPEDTAVYYCAKDPSPYYRGSAYLLSGSYDSWGQGTLVTVSS |
| 23 | WO2011/135026: SEQ ID NO:37 | EVQLLESGGGLVQPGGSLRLSCAASGRIFSLPASGNIFNLLTIAWYRQAPGKGRELVATINSGSRTYYADSVKGRFTISRDNSKKTVYLQMNSLRPEDTAVYYCAASGFTFSSFQMSWVRQAPGKGLEWVSSISGSGSDTLYADSVKGRFTISRDNAKTTLYLQMNSLRPEDTAVYYCTIGGSLSRSSQGTLVTVSSGGGGSGGGGSEVQLLESGGGLVQPGGSLRLSCAASGRTLSSYAMGWFRQAPGKGREFVARISQGGTAIYYADSVKGRFTISRDNSKNTVYLQMNSLRPEDTAVYYCAKDPSPYYRGSAYLLSGSYDSWGQGTLVTVSS |

Figure 2

| Numbering according to Kabat (VH) | Numbering according to Chothia (VH) | Aho numbering | IMGT |
|---|---|---|---|
| 11 | 11 | 12 | 12 |
| 14 | 14 | 15 | 15 |
| 41 | 41 | 48 | 46 |
| 42 | 42 | 49 | 47 |
| 87 | 87 | 101 | 99 |
| 89 | 89 | 103 | 101 |
| 108 | 108 | 144 | --- |
| 110 | 110 | 146 | --- |
| 112 | 112 | 148 | --- |

Source: http://www.bioc.uzh.ch/plueckthun/antibody/Numbering/NumFrame.html

| | Normalized Pre-Ab binding levels (RU at 125) | | | Reduction pre-Ab binding compared to SEQ ID NO:1 (percent) | |
|---|---|---|---|---|---|
| Sample | SEQ ID NO:1 | SEQ ID NO:2 | SEQ ID NO:3 | SEQ ID NO:2 | SEQ ID NO:3 |
| IHuS#ABL-0042-02 | -8 | -12 | -16 | | |
| IHuS#ABL-0088-03 | 316 | 70 | -4 | 78 | 100 |
| IHuS#ABL-0137-01 | 19 | -4 | 6 | | |
| IHuS#ABL-0138-01 | 28 | -13 | -11 | 100 | 100 |
| IHuS#ABL-0139-01 | 71 | -10 | -8 | 100 | 100 |
| IHuS#ABL-0141-01 | 8 | -8 | -5 | | |
| IHuS#ABL-0149-01 | 111 | -14 | -22 | 100 | 100 |
| IHuS#ABL-0150-01 | | 0 | 0 | | |
| IHuS#ABL-0151-01 | 213 | 6 | -4 | 97 | 100 |
| IHuS#ABL-0152-01 | 77 | -11 | -10 | 100 | 100 |
| IHuS#ABL-0153-01 | 262 | 11 | 8 | 96 | 97 |
| IHuS#ABL-0154-01 | -2 | -10 | -9 | | |
| IHuS#ABL-0159-01 | 26 | -10 | -6 | 100 | 100 |
| IHuS#ABL-0160-01 | 2 | -8 | -3 | | |
| IHuS#ABL-0161-01 | 7 | -3 | 1 | | |
| IHuS#ABL-0162-01 | -10 | -15 | -10 | | |
| IHuS#ABL-0148-01 | 505 | -1 | -1 | 100 | 100 |
| IHuS#ABL-0163-01 | 506 | 40 | -4 | 92 | 100 |
| IHuS#ABL-0171-01 | 6 | -13 | -19 | | |
| IHuS#ABL-0172-01 | 143 | 1 | -4 | 99 | 100 |
| IHuS#ABL-0218-01 | 131 | -3 | -3 | 100 | 100 |
| IHuS#ABL-0040-03 | 487 | 22 | -4 | 95 | 100 |
| IHuS#ABL-0090-02 | 702 | 53 | -19 | 92 | 100 |
| IHuS#ABL-0173-01 | 367 | 3 | 4 | 99 | 99 |
| IHuS#ABL-0188-01 | 12 | -11 | -12 | | |
| IHuS#ABL-0006-02 | 728 | 195 | 22 | 73 | 97 |
| IHuS#ABL-0189-01 | 18 | -1 | -3 | | |
| IHuS#ABL-0190-01 | -2 | -11 | -7 | | |
| IHuS#ABL-0191-01 | -6 | -15 | -11 | | |
| IHuS#ABL-0192-01 | 24 | -10 | -11 | 100 | 100 |
| IHuS#ABL-0198-01 | 31 | -6 | -18 | 100 | 100 |
| IHuS#ABL-0165-01 | 350 | 1 | -11 | 100 | 100 |
| IHuS#ABL-0199-01 | 335 | 38 | -4 | 89 | 100 |
| IHuS#ABL-0200-01 | 21 | -14 | -10 | 100 | 100 |
| IHuS#ABL-0201-01 | 64 | 3 | -10 | 95 | 100 |

Figure 6 (continued)

| Sample | SEQ ID NO:1 | SEQ ID NO:2 | SEQ ID NO:3 | SEQ ID NO:2 | SEQ ID NO:3 |
|---|---|---|---|---|---|
| IHuS#ABL-0202-01 | 143 | 32 | -16 | 77 | 100 |
| IHuS#ABL-0044-02 | -15 | -15 | -20 | | |
| IHuS#ABL-0209-01 | 33 | -4 | -2 | 100 | 100 |
| IHuS#ABL-0210-01 | 11 | -10 | -6 | | |
| IHuS#ABL-0211-01 | 58 | -12 | -11 | 100 | 100 |
| IHuS#ABL-0212-01 | 226 | 12 | 16 | 94 | 93 |
| IHuS#ABL-0213-01 | 9 | -12 | -10 | | |
| IHuS#ABL-0183-01 | 528 | 31 | -12 | 94 | 100 |
| IHuS#ABL-0005-06 | 16 | -2 | -11 | | |
| IHuS#ABL-0219-01 | 22 | -10 | -9 | 100 | 100 |
| IHuS#ABL-0221-01 | 42 | -16 | -20 | 100 | 100 |
| IHuS#ABL-0222-01 | 242 | -9 | 0 | 100 | 100 |
| IHuS#ABL-0223-01 | 436 | 2 | -13 | 99 | 100 |
| IHuS#ABL-0142-01 | 34 | -21 | -32 | 100 | 100 |
| IHuS#ABL-0143-01 | 39 | -9 | -4 | 100 | 100 |
| IHuS#ABL-0144-01 | 151 | -8 | -11 | 100 | 100 |
| IHuS#ABL-0145-01 | 146 | -13 | -4 | 100 | 100 |
| IHuS#ABL-0146-01 | 123 | -15 | -11 | 100 | 100 |
| IHuS#ABL-0147-01 | 289 | 0 | -6 | 100 | 100 |
| IHuS#ABL-0031-04 | 0 | 7 | 22 | | |
| IHuS#ABL-0047-02 | 75 | -8 | -10 | 100 | 100 |
| IHuS#ABL-0155-01 | 128 | 5 | -1 | 96 | 100 |
| IHuS#ABL-0156-01 | 114 | -3 | -7 | 100 | 100 |
| IHuS#ABL-0157-01 | 433 | 2 | -1 | 100 | 100 |
| IHuS#ABL-0158-01 | 352 | 0 | -9 | 100 | 100 |
| IHuS#ABL-0164-01 | -12 | -16 | -19 | | |
| IHuS#ABL-0166-01 | -4 | -5 | 1 | | |
| IHuS#ABL-0167-01 | 500 | 16 | -6 | 97 | 100 |
| IHuS#ABL-0168-01 | -12 | -14 | -11 | | |
| IHuS#ABL-0169-01 | 36 | -18 | -18 | 100 | 100 |
| IHuS#ABL-0170-01 | 365 | 6 | -1 | 98 | 100 |
| ABL-0041-01_C | 170 | 4 | -12 | 98 | 100 |
| ABL-0053-01_C | 412 | 9 | -11 | 98 | 100 |
| ABL-0054-01_C | 566 | 16 | -3 | 97 | 100 |
| ABL-0046-01_C | 683 | 91 | 1 | 87 | 100 |
| ABL-0062-01_C | 645 | 28 | 0 | 96 | 100 |
| ABL-0039-01_C | 712 | 99 | 1 | 86 | 100 |

Figure 6 (continued)

| Sample | SEQ ID NO:1 | SEQ ID NO:2 | SEQ ID NO:3 | SEQ ID NO:2 | SEQ ID NO:3 |
|---|---|---|---|---|---|
| HSI#26062008Ind11 | 885 | 331 | 19 | 63 | 96 |
| IHuS#29Sep2011Ind14F | 307 | 67 | -5 | 78 | 100 |
| IHuS#29Sep2011Ind39F | 271 | 3 | -4 | 99 | 100 |
| IHuS#29Sep2011Ind43M | 69 | -10 | -7 | 100 | 100 |
| IHuS#29Sep2011Ind44F | 662 | 50 | -12 | 92 | 100 |
| IHuS#P6012314 A20 | 214 | 3 | -4 | 98 | 100 |
| IHuS#P7012314 A06 | 308 | -66 | -5 | 100 | 100 |
| IHuS#P7012314 A12 | 338 | -1 | -11 | 100 | 100 |
| IHuS#ABL-0195-01 | 497 | 17 | 1 | 97 | 100 |
| IHuS#ABL-0206-01 | 576 | 89 | -4 | 85 | 100 |
| IHuS#ABL-0184-01 | 350 | 17 | 22 | 95 | 94 |
| NB130259-004 | 133 | 8 | 1 | 94 | 99 |
| IHuS#04APR2012Ind05m | 261 | 16 | 17 | 94 | 94 |
| IHuS#04APR2012Ind06m | 362 | 19 | 46 | 95 | 87 |
| IHuS#04APR2012Ind07m | 249 | 8 | 32 | 97 | 87 |
| IHuS#04APR2012Ind09m | 333 | 9 | 42 | 97 | 87 |
| IHuS#04APR2012Ind10m | 435 | 11 | 18 | 98 | 96 |
| IHuS#04APR2012Ind03F | 592 | 50 | -4 | 92 | 100 |
| IHuS#04APR2012Ind04F | 135 | -238 | -317 | 100 | 100 |
| IHuS#04APR2012Ind15F | 490 | 60 | -8 | 88 | 100 |
| IHuS#04APR2012Ind27F | 736 | 72 | 221 | 90 | 70 |
| IHuS#04APR2012Ind29F | 494 | 22 | -1 | 96 | 100 |
| IHuS#04APR2012Ind31F | 466 | 112 | -6 | 76 | 100 |
| IHuS#04APR2012Ind40F | 468 | 10 | -7 | 98 | 100 |

NUCLEIC ACIDS ENCODING POLYPEPTIDES AGAINST IL-23

RELATED APPLICATIONS

This application is a continuation of U.S. application Ser. No. 15/769,864, which is a national stage filing under 35 U.S.C. 371 of International Patent Application Serial No. PCT/EP2016/076076, filed Oct. 28, 2016, which claims the benefit under 35 U.S.C. § 119(e) of U.S. Provisional Application Ser. No. 62/248,468, filed Oct. 30, 2015, the contents of each of which is incorporated by reference herein in its entirety for all purposes.

REFERENCE TO A SEQUENCE LISTING SUBMITTED AS A TEXT FILE VIA EFS-WEB

This application contains a Sequence Listing which has been filed electronically in ASCII format and is hereby incorporated herein by reference in its entirety. This ASCII copy, created on Feb. 18, 2021, is named A084870183US02-SEQ-JRV and is 78.418 KB in size.

DESCRIPTION

The present invention relates to amino acid sequences that are directed against IL-23.

The amino acid sequences of the present invention comprise two NANOBODIES® (immunoglobulin single variable domains) against IL-23 and one NANOBODY® (immunoglobulin single variable domain) against serum albumin, linked by two linkers (9GS linkers).

In particular, the invention relates to the amino acid sequences of SEQ ID NO: 2 and SEQ ID NO: 3 (listed in Table 1 and FIG. 1) (also referred to herein as "anti-IL 23 polypeptides of the invention").

TABLE 1

| Polypeptides of the invention | |
|---|---|
| SEQ ID NO: 2 | DVQLLESGGGVVQPGGSLRLSCAASGRIFS LPASGNIFNLLTIAWYRQAPGKGRELVATI NSGSRTYYADSVKGRFTISRDNSKKTVYLQ MNSLRPEDTALYYCQTSGSGSPNFWGQGTL VTVSSGGGSGGGSEVQLVESGGGVVQPGN SLRLSCAASGFTFSSFGMSWVRQAPGKGLE WVSSISGSGSDTLYADSVKGRFTISRDNAK TTLYLQMNSLRPEDTALYYCTIGGSLSRSS QGTLVTVSSGGGGSGGGSEVQLLESGGGVV QPGGSLRLSCAASGRTLSSYAMGWFRQAPG KGREFVARISQGGTAIYYADSVKGRFTISR DNSKNTLYLQMNSLRPEDTALYYCAKDPSP YYRGSAYLLSGSYDSWGQGTLVTVSSA |
| SEQ ID NO: 3 | DVQLLESGGGVVQPGGSLRLSCAASGRIFS LPASGNIFNLLTIAWYRQAPGKGRELVATI NSGSRTYYADSVKGRFTISRDNSKKTVYLQ MNSLRPEDTALYYCQTSGSGSPNFWGQGTL VKVSSGGGGSGGGSEVQLVESGGGVVQPGN SLRLSCAASGFTFSSFGMSWVRQAPGKGLE WVSSISGSGSDTLYADSVKGRFTISRDNAK TTLYLQMNSLRPEDTALYYCTIGGSLSRSS QGTLVKVSSGGGGSGGGSEVQLLESGGGVV QPGGSLRLSCAASGRTLSSYAMGWFRQAPG KGREFVARISQGGTAIYYADSVKGRFTISR DNSKNTLYLQMNSLRPEDTALYYCAKDPSP YYRGSAYLLSGSYDSWGQGTLVKVSSA |

Other aspects, embodiments, features, uses and advantages of the invention will be clear to the skilled person based on the disclosure herein.

In the present application, the amino acid residues/positions in an immunoglobulin heavy-chain variable domain will be indicated with the numbering according to Kabat. For the sake of convenience, FIG. 2 gives a table listing some of the amino acid positions that will be specifically referred to herein and their numbering according to some alternative numbering systems (such as Aho and IMGT. Note: unless explicitly indicated otherwise, for the present description and claims, Kabat numbering is decisive; other numbering systems are given for reference only).

Amino acid sequences against IL-23 based on related NANOBODY® building blocks are known from WO 2009/068627, WO 2010/142534 and WO2011/135026. These prior art sequences are given in Table 1 as SEQ ID NO's: 4 to 23. FIG. 3 shows an alignment of these prior art sequences with the sequences of SEQ ID NO: 2 and SEQ ID NO: 3 according to the invention (the sequence of SEQ ID NO:1 is a reference sequence that has been included for the purpose of making the alignment, i.e. in order to clearly show the amino acid "differences" between the amino acid sequences of the invention and the prior art sequences of SEQ ID NO:s 4 to 23. SEQ ID NO: 1 corresponds to the prior art sequence of SEQ ID NO:22, but with an N-terminal Asp-residue (D) instead of an N-terminal Glu-residue (E). This reference sequence is also used as a comparator in Example 1.

Compared to the amino acid sequences of SEQ ID NOs: 4 to 23, the anti-IL 23 polypeptides of the invention contain a number of specific amino acid residues/mutations (shown in the alignment of FIG. 3), as well as a C-terminal alanine residue. As a result of the presence of these mutations and alanine-extension, the amino acid residues of the invention show much reduced binding by so-called "pre-existing antibodies" (for which reference is made WO 12/175741, WO 2013/024059 and also for example by Holland et al. (J. Clin. Immunol. 2013, 33(7):1192-203) as well as to the co-pending non-prepublished PCT application PCT/EP2015/060643 by Assignee filed on May 13, 2015 and entitled "Improved immunoglobulin variable domains" (published on Nov. 19, 2015 as WO 2015/173325) compared to the prior art sequences of SEQ ID NO's 4 to 23.

All terms not explicitly defined herein are as defined in WO 2009/068627.

In a first aspect, the invention relates to an amino acid sequence that is chosen from the amino acid sequences of SEQ ID NO: 2 and SEQ ID NO: 3. These amino acid sequences can bind to (and can in particular specifically bind to, as defined in WO 2009/068627) IL-23 and/or can modulate signaling mediated by IL-23 (or its receptor) and they can be used to prevent or treat diseases associated with IL-23 (as described herein and in WO 2009/068627, WO 2010/142534 and WO2011/135026).

In a specific aspect, the invention relates to an amino acid sequence that is the amino acid sequence of SEQ ID NO: 2.

In yet another specific aspect, the invention relates to an amino acid sequence that is the amino acid sequence of SEQ ID NO: 3.

It will be clear to the skilled person from the disclosure herein that the anti-IL-23 polypeptides of the invention are directed against (as defined WO 2009/068627) IL-23 and are improved variants of the prior art sequences referred to herein. Thus, the anti-IL-23 polypeptides of the invention can be used for the same purposes, uses and applications as the prior art sequences, for example to modulate signaling that is mediated by IL-23 and/or its receptor(s); and/or in the prevention or treatment of diseases associated with IL-23 and/or with signaling that is mediated by IL-23, such as for example inflammation and inflammatory disorders such as bowel diseases (ulcerative colitis, Crohn's disease, IBD), infectious diseases, psoriasis, cancer, autoimmune diseases (such as MS), sarcoidosis, transplant rejection, cystic fibrosis, asthma, chronic obstructive pulmonary disease, rheumatoid arthritis, viral infection, common variable immunodeficiency, and the various diseases and disorders mentioned in the prior art cited herein. Further reference is again made to WO 2009/068627, WO 2010/142534 and WO2011/135026.

For example, as mentioned on pages 4-5 of WO 09/068627, IL23 was shown to be responsible for the chronic inflammation observed in inflammatory bowel disease. This was confirmed by the fact that the IL23R gene was identified as being involved in inflammatory bowel disease. It has also been found that p19 knock out mice are resistant to collagen-induced arthritis and colitis, whereas comparable p35 knock out mice were found to be more susceptible to collagen-induced arthritis. Also, when p19 knock out mice were crossed with IL-10 knock out mice, the resulting offspring were resistant to colitis, whereas similar crosses of p19 knock out mice with IL-10 knock out mice resulted in offspring that was susceptible to colitis. It was further found that a monoclonal antibody against p19 inhibits the development of EAE, a preclinical animal model for multiple sclerosis, and reduces serum levels of IL-17 (which is not regulated by IL-12). Also, IL-23 rather than IL-12 appears to be the essential cytokine in CNS autoimmune inflammation. All this results suggests that IL-23/p19 may be an attractive target for the treatment of colitis, Crohn's diseases, IBD, multiple sclerosis, rheumatoid arthritis and some of the other diseases and disorders mentioned herein. Also, IL23 and IL27—two of the other heterodimeric cytokines from the IL-12 family—also regulate TH1-cell response, albeit with distinct functions. The ability of IL-23 to stimulate CD4+ T cells to produce IL-17 also has been described as having a dominant role in the development and maintenance of autoimmune inflammation.

Also, Example 45 of WO 09/068627 shows that the polypeptides of WO 09/068627 (and thus, by extension, the anti-IL-23 polypeptides of the invention) can also be valuable in the prevention and treatment of psoriasis (either by systemic/parenteral administration or by topical treatment, e.g. using a crème or lotion (see page 328 and 331-332 of WO 09/068627).

In another aspect, the invention relates to a nucleic acid that encodes an anti-IL-23 polypeptide of the invention. Such a nucleic acid will also be referred to herein as a "nucleic acid of the invention".

In another aspect, the invention relates to a host or host cell that expresses (or that under suitable circumstances is capable of expressing) an anti-IL-23 polypeptide of the invention; and/or that contains a nucleic acid of the invention. Such a host or host cell may again generally be as described in WO 09/068627 (see for example pages 315-328).

The invention also relates to methods for the production/expression of an anti-IL-23 polypeptide of the invention. Such methods may generally comprise the steps of (i) the expression, in a suitable host cell or host organism or in another suitable expression system of a nucleic acid that encodes an anti-IL-23 polypeptide of the invention, optionally followed by: (ii) isolating and/or purifying the anti-IL-23 polypeptide of the invention thus obtained. In particular, such a method may comprise the steps of (i) cultivating and/or maintaining a host of the invention under conditions that are such that said host of the invention expresses and/or produces an anti-IL-23 polypeptide of the invention; optionally followed by (ii) isolating and/or purifying the anti-IL-23 polypeptide of the invention thus obtained. These methods again may essentially be performed as described in WO 09/068627 (see for example pages 315-328).

One specific method for the production/expression of the anti-IL-23 polypeptides of the invention is described in the International application of Ablynx N.V. entitled "Method for the production of domain antibodies", which has an international filing date of Apr. 30, 2010.

The invention further relates to a product or composition containing or comprising an anti-IL-23 polypeptide of the invention and/or at least one nucleic acid of the invention, and optionally one or more further components of such compositions known per se, i.e. depending on the intended use of the composition. Such a product or composition may for example be a pharmaceutical composition (as described herein), a veterinary composition or a product or composition for diagnostic use (as also described herein). Such products or compositions may again generally be as described in WO 09/068627 (see for example pages 329-337).

The invention also relates to the use of an anti-IL-23 polypeptide of the invention, or of a composition comprising the same, in (methods or compositions for) modulating (as defined in WO 09/068627) IL-23 and/or IL-23-mediated signaling (as defined in WO 09/068627), either in vitro (e.g. in an in vitro or cellular assay) or in vivo (e.g. in an a single cell or in a multicellular organism, and in particular in a mammal, and more in particular in a human being, such as in a human being that is at risk of or suffers from a disease or disorder associated with heterodimeric cytokines and their receptors).

The invention also relates to methods for modulating (as defined in WO 09/068627) IL-23 and/or IL-23-mediated signaling (as defined in WO 09/068627), either in vitro (e.g. in an in vitro or cellular assay) or in vivo (e.g. in an a single cell or multicellular organism, and in particular in a mammal, and more in particular in a human being, such as in a human being that is at risk of or suffers from a disease or disorder associated with IL-23 and/or its receptors), which method comprises at least the step of contacting IL-23 with an anti-IL-23 polypeptide of the invention, in a manner and in an amount suitable to modulate IL-23 and/or IL-23-mediated signaling.

The invention also relates to the use of an anti-IL-23 polypeptide of the invention in the preparation of a composition (such as, without limitation, a pharmaceutical composition or preparation as further described herein) for modulating (as defined in WO 09/068627) IL-23 and/or IL-23-mediated signaling (as defined in WO 09/068627), either in vitro (e.g. in an in vitro or cellular assay) or in vivo (e.g. in an a single cell or multicellular organism, and in particular in a mammal, and more in particular in a human being, such as in a human being that is at risk of or suffers from a disease or disorder associated with IL-23 and/or IL-23 mediated signaling).

The invention also relates to an anti-IL-23 polypeptide of the invention (or a composition comprising the same) for use in modulating signaling that is mediated by IL-23 and/or its receptor(s).

The invention also relates to an anti-IL-23 polypeptide of the invention (or a composition comprising the same) for use in the prevention or treatment of diseases associated with IL-23 and/or with signaling that is mediated by IL-23, such as for example inflammation and inflammatory disorders such as bowel diseases (ulcerative colitis, Crohn's disease, IBD), infectious diseases, psoriasis, cancer, autoimmune diseases (such as MS), sarcoidosis, transplant rejection, cystic fibrosis, asthma, chronic obstructive pulmonary disease, rheumatoid arthritis, viral infection, common variable immunodeficiency.

The invention also relates to a method for preventing or treating a disease associated with IL-23 and/or with signaling that is mediated by IL-23, such as for example inflammation and inflammatory disorders such as bowel diseases (ulcerative colitis, Crohn's disease, IBD), infectious diseases, psoriasis, cancer, autoimmune diseases (such as MS), sarcoidosis, transplant rejection, cystic fibrosis, asthma, chronic obstructive pulmonary disease, rheumatoid arthritis, viral infection, common variable immunodeficiency, said method comprising administering to a subject in need of such treatment a prophylactic or therapeutically active amount of an anti-IL-23 polypeptide of the invention (or of a composition comprising the same).

The invention will now be further described by means of the following non-limiting preferred aspects, examples and figures, in which:

FIG. 1 lists the amino acid sequences referred to herein (SEQ ID NOs:1-23, see left column). The second column from left lists the reference SEQ ID NOs of the sequences if they appeared in previous applications, i.e., in WO 2009/068627, WO 2010/142534, or WO2011/135026;

FIG. 2 is a table listing some of the amino acid positions that will be specifically referred to herein and their numbering according to some alternative numbering systems (such as Aho and IMGT);

Figure 3:
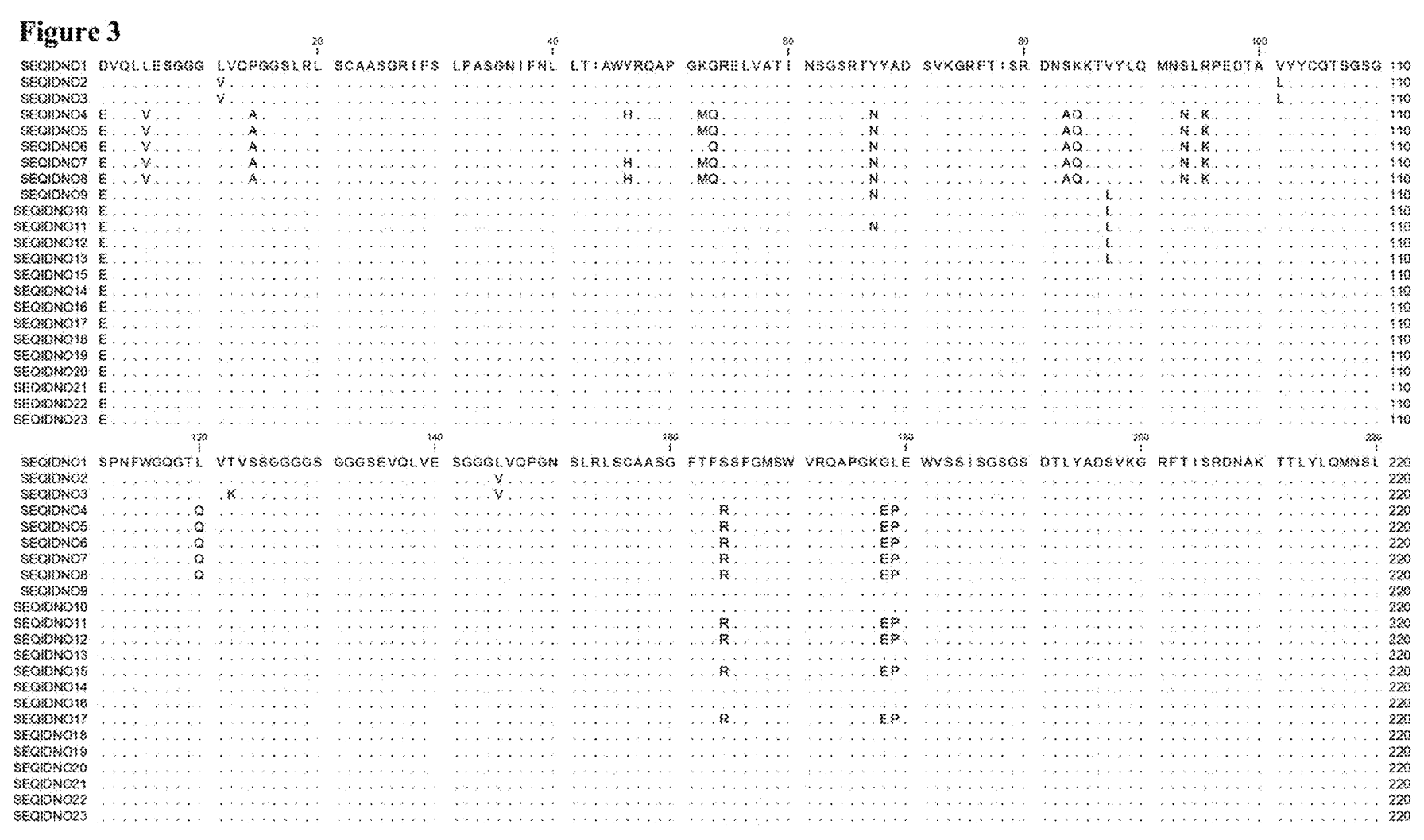

FIG. 3 shows an alignment of the amino acid sequences referred to herein.

Figure 4:
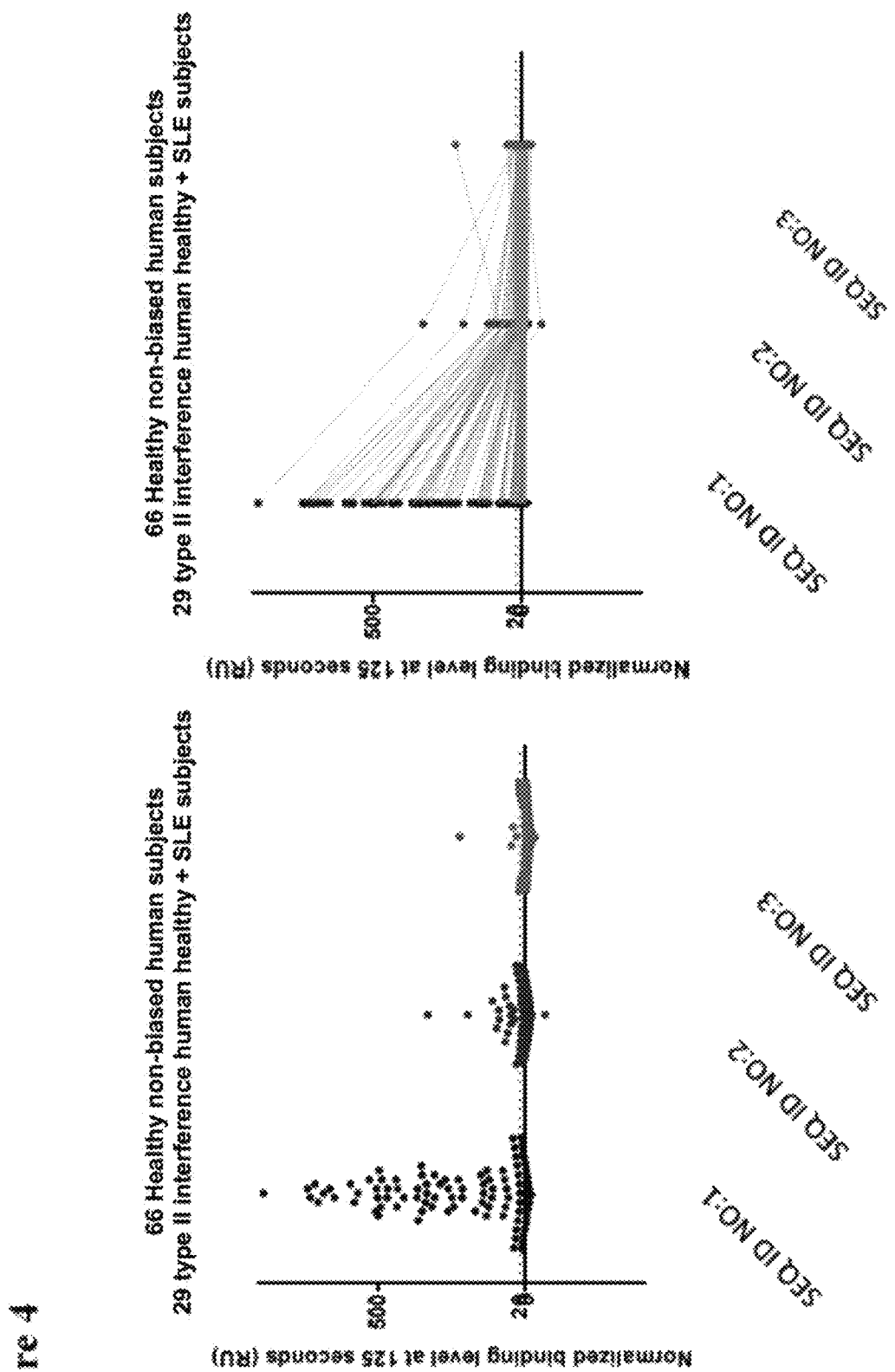
Figure 5:
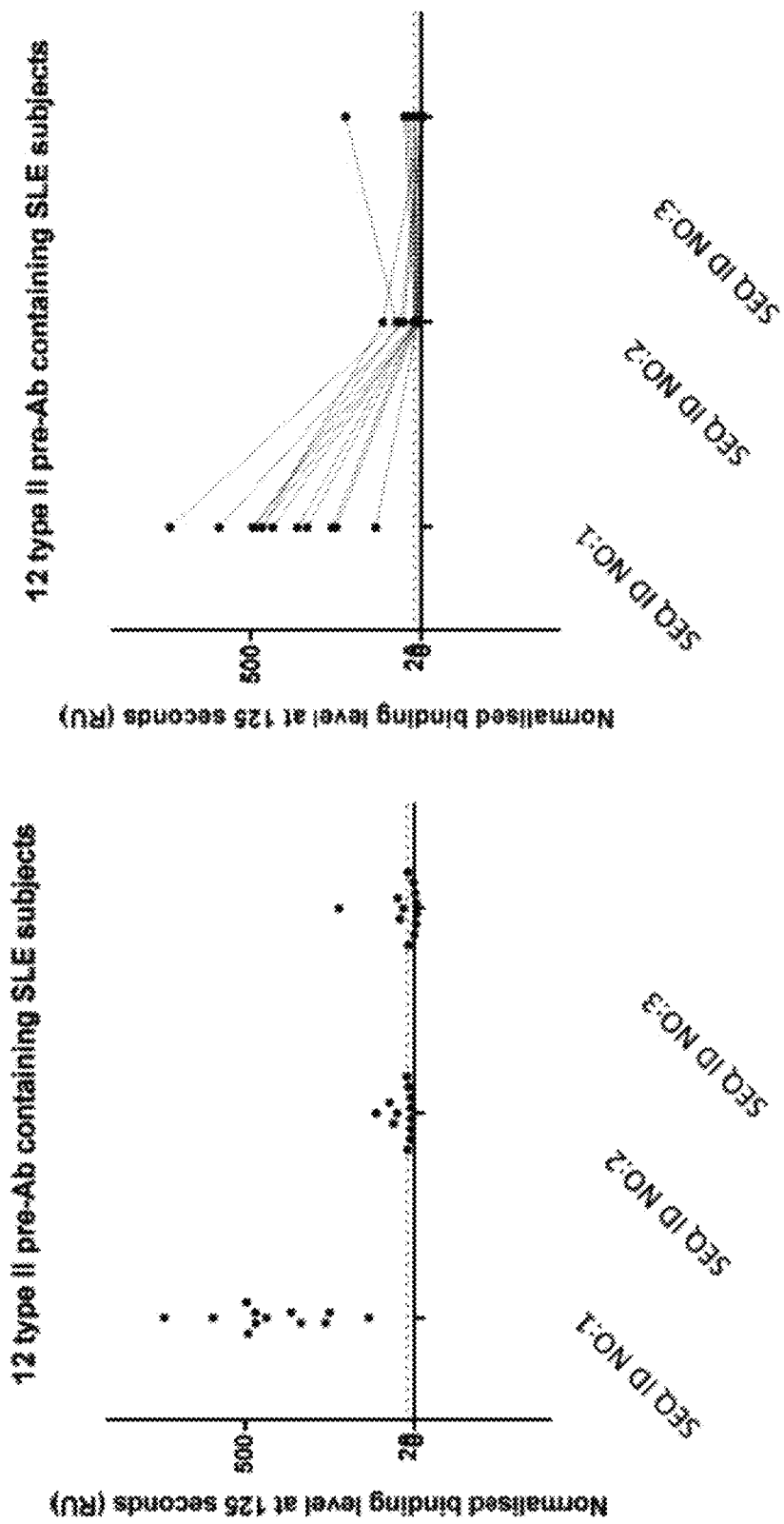

FIG. 4 shows two corresponding plots of data points obtained in Example 1 when 66 serum samples from human healthy subjects and 29 samples from SLE patients were tested for binding to SEQ ID NO:1 (reference) and SEQ ID NOs: 2 and 3 (invention). Each dot represents the binding level for one of the 96 samples tested. The data points shown in the right hand panel and the left hand panel are the same; in the right hand panel the data points measured with each individual sample for each of the three compounds tested (i.e. SEQ ID NO:1, SEQ ID NO:2 and SEQ ID NO:3, respectively) are connected by means of a line (as a result, the declination of the line gives an indication of the extent to which binding by pre-existing antibodies is reduced when the mutations of the invention and the C-terminal alanine are introduced);

FIG. 5 details the data for binding to SEQ ID NO:1 (reference) and SEQ ID NOs: 2 and 3 (invention) of pre-existing antibodies from 10 representative samples from SLE patients tested in Example 1 and shown in FIG. 4.

FIG. 6 is a table listing the binding data (3 columns giving normalized Pre-existing antibody ("Pre-Ab") binding levels (RU at 125) and 2 columns giving percentage of reduction in Pre-existing antibody binding compared to SEQ ID NO:1, respectively) of the data points compiled in FIG. 4.

EXPERIMENTAL PART

The human samples used in the Experimental Part below were either obtained from commercial sources or from human volunteers (after all required consents and approvals were obtained) and were used in according with the applicable legal and regulatory requirements (including but not limited to those regarding medical secret and patient privacy)

In the Examples below, unless explicitly indicated otherwise, the binding of pre-existing antibodies that are present in the samples used (i.e. from healthy volunteers, and SLE patients) to the NANOBODIES® tested was determined using PROTEON™ (protein interaction analysis system) as follows:

NANOBODIES® were captured on human serum albumin and the binding of pre-existing antibodies on the captured NANOBODIES® was evaluated using the PROTEON™ XPR36 (Bio-Rad Laboratories, Inc.). PBS/TWEEN® (polyethylene glycol sorbitan monolaurate) (phosphate buffered saline, pH7.4, 0.005% TWEEN®20) was used as running buffer and the experiments were performed at 25° C. The ligand lanes of a PROTEON™ GLC Sensor Chip were activated with EDC/NHS (flow rate 30 µl/min) and HSA was injected at 10 µg/ml in PROTEON™ Acetate buffer pH4.5 (flow rate 100 µl/min) to render immobilization levels of approximately 3200 RU. After immobilization, surfaces were deactivated with ethanolamine HCl (flow rate 30 µl/min). NANOBODIES® were injected for 2 minutes at 45 µl/min over the HSA surface to render a NANOBODY® capture level of approximately 600 RU. The samples containing pre-existing antibodies were centrifuged for 2 minutes at 14,000 rpm and supernatant was diluted 1:10 in PBS-TWEEN®20 (0.005%) before being injected for 2 minutes at 45 µl/min followed by a subsequent 400 seconds dissociation step. After each cycle (i.e. before a new NANOBODY® capture and blood sample injection step) the HSA surfaces were regenerated with a 2 minute injection of HCl (100 mM) at 45 µl/min. Sensorgram processing and data analysis was performed with PROTEON™ Manager 3.1.0 (Bio-Rad Laboratories, Inc.). Sensorgrams showing pre-existing antibody binding were obtained after double referencing by subtracting 1) NANOBODY®-HSA dissociation and 2) non-specific binding to reference ligand lane. Binding levels of pre-existing antibodies were determined by setting report points at 125 seconds (5 seconds after end of association). Percentage reduction in pre-existing antibody binding was calculated relative to the binding levels at 125 seconds of a reference NANOBODY®.

Example 1

Binding of Pre-Existing Antibodies to SEQ ID NO:1 (Reference), SEQ ID NO:2 (Invention) and SEQ ID NO:3 (Invention)

The amino acid sequences of SEQ ID NO:1 (reference), SEQ ID NO:2 (invention) and SEQ ID NO:3 (invention) were tested for binding by pre-existing antibodies present in serum samples obtained from 66 healthy human volunteers and 29 SLE patients using PROTEON™ using the protocol described in the preamble to the Experimental Part. The sequences tested were captured using human serum albumin.

The results are shown in FIG. 4. FIG. 5 details the results obtained for 12 representative SLE samples (i.e. taken from the 29 tested SLE samples). FIG. 6 gives the data shown in FIG. 4.

The results show that the compounds of SEQ ID NOs: 2 and 3 show much reduced binding by pre-existing antibodies compared to the compound of SEQ ID NO:1 in a large number of samples obtained from healthy human volunteers as well as samples from SLE patients.

The invention claimed is:

1. A nucleic acid that encodes an anti-interleukin 23 (IL-23) polypeptide comprising an amino acid sequence that is chosen from the amino acid sequences of SEQ ID NO: 2 and SEQ ID NO: 3.

2. A nucleic acid that encodes an anti-interleukin 23 (IL-23) polypeptide comprising the amino acid sequence of SEQ ID NO: 2.

3. A nucleic acid that encodes an anti-interleukin 23 (IL-23) polypeptide comprising the amino acid sequence of SEQ ID NO: 3.

4. A non-human host or an isolated host cell that comprises the nucleic acid of claim 1.

5. A non-human host or an isolated host cell that comprises the nucleic acid of claim 2.

6. A non-human host or an isolated host cell that comprises the nucleic acid of claim 3.

7. A method for producing an anti-IL-23 polypeptide, wherein said method comprises
expressing the anti-IL-23 polypeptide encoded by the nucleic acid of claim 1 in a non-human host or an isolated host cell.

8. The method of claim 7, further comprising isolating and/or purifying the anti-IL-23 polypeptide.

9. A method for producing an anti-IL-23 polypeptide, wherein said method comprises cultivating the non-human host or isolated host cell of claim 4 under conditions that are such that said non-human host or isolated host cell expresses the anti-IL-23 polypeptide encoded by the nucleic acid.

10. The method of claim 9, further comprising isolating and/or purifying the anti-IL-23 polypeptide.

11. A method for producing an anti-IL-23 polypeptide, wherein said method comprises maintaining the non-human host or isolated host cell of claim 4 under conditions that are such that said non-human host or isolated host cell expresses the anti-IL-23 polypeptide encoded by the nucleic acid.

12. The method of claim 11, further comprising isolating and/or purifying the anti-IL-23 polypeptide.

* * * * *

SEQUENCE LISTING

<160> NUMBER OF SEQ ID NOS: 23

<210> SEQ ID NO 1
<211> LENGTH: 386
<212> TYPE: PRT
<213> ORGANISM: Artificial Sequence
<220> FEATURE:
<223> OTHER INFORMATION: CDR sequence

<400> SEQUENCE: 1

```
Asp Val Gln Leu Leu Glu Ser Gly Gly Gly Leu Val Gln Pro Gly Gly
1               5                   10                  15

Ser Leu Arg Leu Ser Cys Ala Ala Ser Gly Arg Ile Phe Ser Leu Pro
            20                  25                  30

Ala Ser Gly Asn Ile Phe Asn Leu Leu Thr Ile Ala Trp Tyr Arg Gln
        35                  40                  45

Ala Pro Gly Lys Gly Arg Glu Leu Val Ala Thr Ile Asn Ser Gly Ser
    50                  55                  60

Arg Thr Tyr Tyr Ala Asp Ser Val Lys Gly Arg Phe Thr Ile Ser Arg
65                  70                  75                  80

Asp Asn Ser Lys Lys Thr Val Tyr Leu Gln Met Asn Ser Leu Arg Pro
                85                  90                  95

Glu Asp Thr Ala Val Tyr Tyr Cys Gln Thr Gly Ser Gly Ser Pro
            100                 105                 110

Asn Phe Trp Gly Gln Gly Thr Leu Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
                165                 170                 175

Lys Gly Leu Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser Gly Gly Gly Ser Gly Gly
                245                 250                 255

Gly Ser Glu Val Gln Leu Leu Glu Ser Gly Gly Gly Leu Val Gln Pro
            260                 265                 270

Gly Gly Ser Leu Arg Leu Ser Cys Ala Ala Ser Gly Arg Thr Leu Ser
        275                 280                 285

Ser Tyr Ala Met Gly Trp Phe Arg Gln Ala Pro Gly Lys Gly Arg Glu
    290                 295                 300

Phe Val Ala Arg Ile Ser Gln Gly Gly Thr Ala Ile Tyr Tyr Ala Asp
305                 310                 315                 320

Ser Val Lys Gly Arg Phe Thr Ile Ser Arg Asp Asn Ser Lys Asn Thr
                325                 330                 335

Leu Tyr Leu Gln Met Asn Ser Leu Arg Pro Glu Asp Thr Ala Val Tyr
            340                 345                 350
```

```
Tyr Cys Ala Lys Asp Pro Ser Pro Tyr Tyr Arg Gly Ser Ala Tyr Leu
            355                 360                 365

Leu Ser Gly Ser Tyr Asp Ser Trp Gly Gln Gly Thr Leu Val Thr Val
    370                 375                 380

Ser Ser
385

<210> SEQ ID NO 2
<211> LENGTH: 387
<212> TYPE: PRT
<213> ORGANISM: Artificial Sequence
<220> FEATURE:
<223> OTHER INFORMATION: CDR sequence

<400> SEQUENCE: 2

Asp Val Gln Leu Leu Glu Ser Gly Gly Val Val Gln Pro Gly Gly
1               5                   10                  15

Ser Leu Arg Leu Ser Cys Ala Ala Ser Gly Arg Ile Phe Ser Leu Pro
            20                  25                  30

Ala Ser Gly Asn Ile Phe Asn Leu Leu Thr Ile Ala Trp Tyr Arg Gln
            35                  40                  45

Ala Pro Gly Lys Gly Arg Glu Leu Val Ala Thr Ile Asn Ser Gly Ser
        50                  55                  60

Arg Thr Tyr Tyr Ala Asp Ser Val Lys Gly Arg Phe Thr Ile Ser Arg
65              70                  75                  80

Asp Asn Ser Lys Lys Thr Val Tyr Leu Gln Met Asn Ser Leu Arg Pro
                85                  90                  95

Glu Asp Thr Ala Leu Tyr Tyr Cys Gln Thr Ser Gly Ser Gly Ser Pro
            100                 105                 110

Asn Phe Trp Gly Gln Gly Thr Leu Val Thr Val Ser Ser Gly Gly Gly
        115                 120                 125

Gly Ser Gly Gly Gly Ser Glu Val Gln Leu Val Glu Ser Gly Gly Gly
    130                 135                 140

Val Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
                165                 170                 175

Lys Gly Leu Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
    210                 215                 220

Thr Ala Leu Tyr Tyr Cys Thr Ile Gly Gly Ser Leu Ser Arg Ser Ser
225                 230                 235                 240

Gln Gly Thr Leu Val Thr Val Ser Ser Gly Gly Gly Ser Gly Gly
                245                 250                 255

Gly Ser Glu Val Gln Leu Leu Glu Ser Gly Gly Gly Val Val Gln Pro
            260                 265                 270

Gly Gly Ser Leu Arg Leu Ser Cys Ala Ala Ser Gly Arg Thr Leu Ser
        275                 280                 285

Ser Tyr Ala Met Gly Trp Phe Arg Gln Ala Pro Gly Lys Gly Arg Glu
    290                 295                 300

Phe Val Ala Arg Ile Ser Gln Gly Gly Thr Ala Ile Tyr Tyr Ala Asp
305                 310                 315                 320
```

-continued

```
Ser Val Lys Gly Arg Phe Thr Ile Ser Arg Asp Asn Ser Lys Asn Thr
            325                 330                 335

Leu Tyr Leu Gln Met Asn Ser Leu Arg Pro Glu Asp Thr Ala Leu Tyr
        340                 345                 350

Tyr Cys Ala Lys Asp Pro Ser Pro Tyr Tyr Arg Gly Ser Ala Tyr Leu
            355                 360                 365

Leu Ser Gly Ser Tyr Asp Ser Trp Gly Gln Gly Thr Leu Val Thr Val
        370                 375                 380

Ser Ser Ala
385

<210> SEQ ID NO 3
<211> LENGTH: 387
<212> TYPE: PRT
<213> ORGANISM: Artificial Sequence
<220> FEATURE:
<223> OTHER INFORMATION: CDR sequence

<400> SEQUENCE: 3

Asp Val Gln Leu Leu Glu Ser Gly Gly Gly Val Val Gln Pro Gly Gly
1               5                   10                  15

Ser Leu Arg Leu Ser Cys Ala Ala Ser Gly Arg Ile Phe Ser Leu Pro
            20                  25                  30

Ala Ser Gly Asn Ile Phe Asn Leu Leu Thr Ile Ala Trp Tyr Arg Gln
        35                  40                  45

Ala Pro Gly Lys Gly Arg Glu Leu Val Ala Thr Ile Asn Ser Gly Ser
    50                  55                  60

Arg Thr Tyr Tyr Ala Asp Ser Val Lys Gly Arg Phe Thr Ile Ser Arg
65                  70                  75                  80

Asp Asn Ser Lys Lys Thr Val Tyr Leu Gln Met Asn Ser Leu Arg Pro
                85                  90                  95

Glu Asp Thr Ala Leu Tyr Tyr Cys Gln Thr Ser Gly Ser Gly Ser Pro
            100                 105                 110

Asn Phe Trp Gly Gln Gly Thr Leu Val Lys Val Ser Ser Gly Gly Gly
        115                 120                 125

Gly Ser Gly Gly Gly Ser Glu Val Gln Leu Val Glu Ser Gly Gly Gly
    130                 135                 140

Val Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
                165                 170                 175

Lys Gly Leu Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
    210                 215                 220

Thr Ala Leu Tyr Tyr Cys Thr Ile Gly Gly Ser Leu Ser Arg Ser Ser
225                 230                 235                 240

Gln Gly Thr Leu Val Lys Val Ser Ser Gly Gly Gly Ser Gly Gly
                245                 250                 255

Gly Ser Glu Val Gln Leu Leu Glu Ser Gly Gly Val Val Gln Pro
            260                 265                 270

Gly Gly Ser Leu Arg Leu Ser Cys Ala Ala Ser Gly Arg Thr Leu Ser
        275                 280                 285
```

Ser Tyr Ala Met Gly Trp Phe Arg Gln Ala Pro Gly Lys Gly Arg Glu
290                 295                 300

Phe Val Ala Arg Ile Ser Gln Gly Gly Thr Ala Ile Tyr Tyr Ala Asp
305                 310                 315                 320

Ser Val Lys Gly Arg Phe Thr Ile Ser Arg Asp Asn Ser Lys Asn Thr
            325                 330                 335

Leu Tyr Leu Gln Met Asn Ser Leu Arg Pro Glu Asp Thr Ala Leu Tyr
                340                 345                 350

Tyr Cys Ala Lys Asp Pro Ser Pro Tyr Tyr Arg Gly Ser Ala Tyr Leu
            355                 360                 365

Leu Ser Gly Ser Tyr Asp Ser Trp Gly Gln Thr Leu Val Lys Val
370                 375                 380

Ser Ser Ala
385

<210> SEQ ID NO 4
<211> LENGTH: 386
<212> TYPE: PRT
<213> ORGANISM: Artificial Sequence
<220> FEATURE:
<223> OTHER INFORMATION: CDR sequence

<400> SEQUENCE: 4

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Ile Phe Ser Leu Pro
            20                  25                  30

Ala Ser Gly Asn Ile Phe Asn Leu Leu Thr Ile Ala Trp His Arg Gln
        35                  40                  45

Ala Pro Gly Met Gln Arg Glu Leu Val Ala Thr Ile Asn Ser Gly Ser
    50                  55                  60

Arg Thr Asn Tyr Ala Asp Ser Val Lys Gly Arg Phe Thr Ile Ser Arg
65                  70                  75                  80

Asp Asn Ala Gln Lys Thr Val Tyr Leu Gln Met Asn Asn Leu Lys Pro
                85                  90                  95

Glu Asp Thr Ala Val Tyr Tyr Cys Gln Thr Gly Ser Gly Ser Pro
            100                 105                 110

Asn Phe Trp Gly Gln Gly Thr Gln Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Arg Ser Phe Gly Met Ser Trp Val Arg Gln Ala Pro Gly
                165                 170                 175

Lys Glu Pro Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Lys Pro Glu Asp
    210                 215                 220

Thr Ala Val Tyr Tyr Cys Thr Ile Gly Gly Ser Leu Ser Arg Ser Ser
225                 230                 235                 240

Gln Gly Thr Gln Val Thr Val Ser Ser Gly Gly Gly Gly Ser Gly Gly
                245                 250                 255

Gly Ser Glu Val Gln Leu Val Glu Ser Gly Gly Gly Leu Val Gln Pro
                260                 265                 270

Gly Gly Ser Leu Arg Leu Ser Cys Ile Ala Ser Gly Leu Pro Phe Ser
            275                 280                 285

Thr Lys Ser Met Gly Trp Phe Arg Gln Ala Pro Gly Lys Glu Arg Glu
        290                 295                 300

Phe Val Ala Arg Ile Ser Pro Gly Gly Thr Ser Arg Tyr Tyr Gly Asp
305                 310                 315                 320

Phe Val Lys Gly Arg Phe Ala Ile Ser Arg Asp Asn Ala Lys Asn Thr
                325                 330                 335

Thr Trp Leu Gln Met Asn Ser Leu Lys Ala Glu Asp Thr Ala Val Tyr
            340                 345                 350

Tyr Cys Ala Ser Gly Glu Arg Ser Thr Tyr Ile Gly Ser Asn Tyr Tyr
        355                 360                 365

Arg Thr Asn Glu Tyr Asp Tyr Trp Gly Thr Gly Thr Gln Val Thr Val
    370                 375                 380

Ser Ser
385

<210> SEQ ID NO 5
<211> LENGTH: 386
<212> TYPE: PRT
<213> ORGANISM: Artificial Sequence
<220> FEATURE:
<223> OTHER INFORMATION: CDR sequence

<400> SEQUENCE: 5

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Ile Phe Ser Leu Pro
            20                  25                  30

Ala Ser Gly Asn Ile Phe Asn Leu Leu Thr Ile Ala Trp Tyr Arg Gln
        35                  40                  45

Ala Pro Gly Met Gln Arg Glu Leu Val Ala Thr Ile Asn Ser Gly Ser
    50                  55                  60

Arg Thr Asn Tyr Ala Asp Ser Val Lys Gly Arg Phe Thr Ile Ser Arg
65                  70                  75                  80

Asp Asn Ala Gln Lys Thr Val Tyr Leu Gln Met Asn Asn Leu Lys Pro
                85                  90                  95

Glu Asp Thr Ala Val Tyr Tyr Cys Gln Thr Ser Gly Ser Gly Ser Pro
            100                 105                 110

Asn Phe Trp Gly Gln Gly Thr Gln Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Arg Ser Phe Gly Met Ser Trp Val Arg Gln Ala Pro Gly
                165                 170                 175

Lys Glu Pro Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Lys Pro Glu Asp
    210                 215                 220

```
Thr Ala Val Tyr Tyr Cys Thr Ile Gly Gly Ser Leu Ser Arg Ser Ser
225                 230                 235                 240

Gln Gly Thr Gln Val Thr Val Ser Ser Gly Gly Gly Ser Gly Gly
                245                 250                 255

Gly Ser Glu Val Gln Leu Val Glu Ser Gly Gly Gly Leu Val Gln Ala
                260                 265                 270

Gly Gly Ser Leu Arg Leu Ser Cys Ala Ala Ser Gly Arg Thr Leu Ser
                275                 280                 285

Ser Tyr Ala Met Gly Trp Phe Arg Gln Ala Pro Gly Lys Glu Arg Glu
                290                 295                 300

Phe Val Ala Arg Ile Ser Gln Gly Gly Thr Ala Ile Tyr Tyr Ala Asp
305                 310                 315                 320

Ser Val Lys Gly Arg Phe Thr Ile Ser Arg Asp Asn Ala Lys Asn Thr
                325                 330                 335

Val Tyr Leu Gln Met Asn Ser Leu Lys Pro Glu Asp Thr Ala Val Tyr
                340                 345                 350

Tyr Cys Ala Lys Asp Pro Ser Pro Tyr Arg Gly Ser Ala Tyr Leu
                355                 360                 365

Leu Ser Gly Ser Tyr Asp Ser Trp Gly Gln Gly Thr Gln Val Thr Val
370                 375                 380

Ser Ser
385

<210> SEQ ID NO 6
<211> LENGTH: 386
<212> TYPE: PRT
<213> ORGANISM: Artificial Sequence
<220> FEATURE:
<223> OTHER INFORMATION: CDR sequence

<400> SEQUENCE: 6

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Ile Phe Ser Leu Pro
                20                  25                  30

Ala Ser Gly Asn Ile Phe Asn Leu Leu Thr Ile Ala Trp Tyr Arg Gln
                35                  40                  45

Ala Pro Gly Lys Gln Arg Glu Leu Val Ala Thr Ile Asn Ser Gly Ser
50                  55                  60

Arg Thr Asn Tyr Ala Asp Ser Val Lys Gly Arg Phe Thr Ile Ser Arg
65                  70                  75                  80

Asp Asn Ala Gln Lys Thr Val Tyr Leu Gln Met Asn Asn Leu Lys Pro
                85                  90                  95

Glu Asp Thr Ala Val Tyr Tyr Cys Gln Thr Ser Gly Ser Gly Ser Pro
                100                 105                 110

Asn Phe Trp Gly Gln Gly Thr Gln Val Thr Val Ser Ser Gly Gly Gly
                115                 120                 125

Gly Ser Gly Gly Gly Ser Glu Val Gln Leu Val Ser Gly Gly Gly
                130                 135                 140

Leu Val Gln Pro Gly Asn Ser Leu Arg Leu Ser Cys Ala Ala Ser Gly
145                 150                 155                 160

Phe Thr Phe Arg Ser Phe Gly Met Ser Trp Val Arg Gln Ala Pro Gly
                165                 170                 175

Lys Glu Pro Glu Trp Val Ser Ser Ile Ser Gly Ser Gly Ser Asp Thr
                180                 185                 190
```

```
Leu Tyr Ala Asp Ser Val Lys Gly Arg Phe Thr Ile Ser Arg Asp Asn
            195                 200                 205

Ala Lys Thr Thr Leu Tyr Leu Gln Met Asn Ser Leu Lys Pro Glu Asp
    210                 215                 220

Thr Ala Val Tyr Tyr Cys Thr Ile Gly Gly Ser Leu Ser Arg Ser Ser
225                 230                 235                 240

Gln Gly Thr Gln Val Thr Val Ser Ser Gly Gly Gly Ser Gly Gly Gly
                245                 250                 255

Gly Ser Glu Val Gln Leu Val Glu Ser Gly Gly Gly Leu Val Gln Ala
            260                 265                 270

Gly Gly Ser Leu Arg Leu Ser Cys Ala Ala Ser Gly Arg Thr Leu Ser
    275                 280                 285

Ser Tyr Ala Met Gly Trp Phe Arg Gln Ala Pro Gly Lys Glu Arg Glu
290                 295                 300

Phe Val Ala Arg Ile Ser Gln Gly Gly Thr Ala Ile Tyr Tyr Ala Asp
305                 310                 315                 320

Ser Val Lys Gly Arg Phe Thr Ile Ser Arg Asp Asn Ala Lys Asn Thr
                325                 330                 335

Val Tyr Leu Gln Met Asn Ser Leu Lys Pro Glu Asp Thr Ala Val Tyr
            340                 345                 350

Tyr Cys Ala Lys Asp Pro Ser Pro Tyr Tyr Arg Gly Ser Ala Tyr Leu
    355                 360                 365

Leu Ser Gly Ser Tyr Asp Ser Trp Gly Gln Gly Thr Gln Val Thr Val
370                 375                 380

Ser Ser
385

<210> SEQ ID NO 7
<211> LENGTH: 386
<212> TYPE: PRT
<213> ORGANISM: Artificial Sequence
<220> FEATURE:
<223> OTHER INFORMATION: CDR sequence

<400> SEQUENCE: 7

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Ile Phe Ser Leu Pro
            20                  25                  30

Ala Ser Gly Asn Ile Phe Asn Leu Leu Thr Ile Ala Trp His Arg Gln
        35                  40                  45

Ala Pro Gly Met Gln Arg Glu Leu Val Ala Thr Ile Asn Ser Gly Ser
    50                  55                  60

Arg Thr Asn Tyr Ala Asp Ser Val Lys Gly Arg Phe Thr Ile Ser Arg
65                  70                  75                  80

Asp Asn Ala Gln Lys Thr Val Tyr Leu Gln Met Asn Asn Leu Lys Pro
                85                  90                  95

Glu Asp Thr Ala Val Tyr Tyr Cys Gln Thr Ser Gly Ser Gly Ser Pro
            100                 105                 110

Asn Phe Trp Gly Gln Gly Thr Gln Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160
```

```
Phe Thr Phe Arg Ser Phe Gly Met Ser Trp Val Arg Gln Ala Pro Gly
            165                 170                 175
Lys Glu Pro Glu Trp Val Ser Ser Ile Ser Gly Ser Gly Ser Asp Thr
        180                 185                 190
Leu Tyr Ala Asp Ser Val Lys Gly Arg Phe Thr Ile Ser Arg Asp Asn
    195                 200                 205
Ala Lys Thr Thr Leu Tyr Leu Gln Met Asn Ser Leu Lys Pro Glu Asp
210                 215                 220
Thr Ala Val Tyr Tyr Cys Thr Ile Gly Gly Ser Leu Ser Arg Ser Ser
225                 230                 235                 240
Gln Gly Thr Gln Val Thr Val Ser Ser Gly Gly Gly Ser Gly Gly
                245                 250                 255
Gly Ser Glu Val Gln Leu Val Glu Ser Gly Gly Gly Leu Val Gln Ala
            260                 265                 270
Gly Gly Ser Leu Arg Leu Ser Cys Ala Ala Ser Gly Arg Thr Leu Ser
        275                 280                 285
Ser Tyr Ala Met Gly Trp Phe Arg Gln Ala Pro Gly Lys Glu Arg Glu
    290                 295                 300
Phe Val Ala Arg Ile Ser Gln Gly Gly Thr Ala Ile Tyr Tyr Ala Asp
305                 310                 315                 320
Ser Val Lys Gly Arg Phe Thr Ile Ser Arg Asp Asn Ala Lys Asn Thr
                325                 330                 335
Val Tyr Leu Gln Met Asn Ser Leu Lys Pro Glu Asp Thr Ala Val Tyr
            340                 345                 350
Tyr Cys Ala Lys Asp Pro Ser Pro Tyr Tyr Arg Gly Ser Ala Tyr Leu
        355                 360                 365
Leu Ser Gly Ser Tyr Asp Ser Trp Gly Gln Gly Thr Gln Val Thr Val
    370                 375                 380
Ser Ser
385

<210> SEQ ID NO 8
<211> LENGTH: 386
<212> TYPE: PRT
<213> ORGANISM: Artificial Sequence
<220> FEATURE:
<223> OTHER INFORMATION: CDR sequence

<400> SEQUENCE: 8

Glu Val Gln Leu Val Glu Ser Gly Gly Gly Leu Val Gln Ala Gly Gly
1               5                   10                  15
Ser Leu Arg Leu Ser Cys Ala Ala Ser Gly Arg Ile Phe Ser Leu Pro
            20                  25                  30
Ala Ser Gly Asn Ile Phe Asn Leu Leu Thr Ile Ala Trp His Arg Gln
        35                  40                  45
Ala Pro Gly Met Gln Arg Glu Leu Val Ala Thr Ile Asn Ser Gly Ser
    50                  55                  60
Arg Thr Asn Tyr Ala Asp Ser Val Lys Gly Arg Phe Thr Ile Ser Arg
65                  70                  75                  80
Asp Asn Ala Gln Lys Thr Val Tyr Leu Gln Met Asn Asn Leu Lys Pro
                85                  90                  95
Glu Asp Thr Ala Val Tyr Tyr Cys Gln Thr Ser Gly Ser Gly Ser Pro
            100                 105                 110
Asn Phe Trp Gly Gln Gly Thr Gln Val Thr Val Ser Ser Gly Gly Gly
        115                 120                 125
```

-continued

```
Gly Ser Gly Gly Gly Ser Glu Val Gln Leu Val Glu Ser Gly Gly
        130                 135                 140

Leu Val Gln Pro Gly Asn Ser Leu Arg Leu Ser Cys Ala Ala Ser Gly
145                 150                 155                 160

Phe Thr Phe Arg Ser Phe Gly Met Ser Trp Val Arg Gln Ala Pro Gly
                165                 170                 175

Lys Glu Pro Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Lys Pro Glu Asp
210                 215                 220

Thr Ala Val Tyr Tyr Cys Thr Ile Gly Gly Ser Leu Ser Arg Ser Ser
225                 230                 235                 240

Gln Gly Thr Gln Val Thr Val Ser Ser Gly Gly Gly Ser Gly Gly
                245                 250                 255

Gly Ser Glu Val Gln Leu Val Glu Ser Gly Gly Gly Leu Val Gln Ala
            260                 265                 270

Gly Gly Ser Leu Arg Leu Ser Cys Ala Ala Ser Gly Arg Thr Leu Ser
        275                 280                 285

Ser Tyr Ala Met Gly Trp Phe Arg Gln Ala Pro Gly Lys Glu Arg Glu
        290                 295                 300

Phe Val Ala Arg Ile Ser Gln Gly Gly Thr Ala Ile Tyr Tyr Ala Asp
305                 310                 315                 320

Ser Val Lys Gly Arg Phe Thr Ile Ser Arg Asp Asn Ala Lys Asn Thr
                325                 330                 335

Val Tyr Leu Gln Met Asn Ser Leu Lys Pro Glu Asp Thr Ala Val Tyr
            340                 345                 350

Tyr Cys Ala Lys Asp Pro Ser Pro Tyr Tyr Arg Gly Ser Ala Tyr Leu
        355                 360                 365

Leu Ser Gly Ser Tyr Asp Ser Trp Gly Gln Gly Thr Gln Val Thr Val
        370                 375                 380

Ser Ser
385

<210> SEQ ID NO 9
<211> LENGTH: 386
<212> TYPE: PRT
<213> ORGANISM: Artificial Sequence
<220> FEATURE:
<223> OTHER INFORMATION: CDR sequence

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ile Phe Ser Leu Pro
            20                  25                  30

Ala Ser Gly Asn Ile Phe Asn Leu Leu Thr Ile Ala Trp Tyr Arg Gln
        35                  40                  45

Ala Pro Gly Lys Gly Arg Glu Leu Val Ala Thr Ile Asn Ser Gly Ser
    50                  55                  60

Arg Thr Asn Tyr Ala Asp Ser Val Lys Gly Arg Phe Thr Ile Ser Arg
65                  70                  75                  80

Asp Asn Ser Lys Lys Thr Leu Tyr Leu Gln Met Asn Ser Leu Arg Pro
                85                  90                  95
```

```
Glu Asp Thr Ala Val Tyr Tyr Cys Gln Thr Ser Gly Ser Gly Ser Pro
                100                 105                 110

Asn Phe Trp Gly Gln Gly Thr Leu Val Thr Val Ser Ser Gly Gly Gly
            115                 120                 125

Gly Ser Gly Gly Gly Ser Glu Val Gln Leu Val Glu Ser Gly Gly Gly
        130                 135                 140

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
                165                 170                 175

Lys Gly Leu Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser Gly Gly Gly Ser Gly Gly
                245                 250                 255

Gly Ser Glu Val Gln Leu Leu Glu Ser Gly Gly Gly Leu Val Gln Pro
        260                 265                 270

Gly Gly Ser Leu Arg Leu Ser Cys Ala Ala Ser Gly Arg Thr Leu Ser
            275                 280                 285

Ser Tyr Ala Met Gly Trp Phe Arg Gln Ala Pro Gly Lys Gly Arg Glu
        290                 295                 300

Phe Val Ser Arg Ile Ser Gln Gly Gly Thr Ala Ile Tyr Tyr Ala Asp
305                 310                 315                 320

Ser Val Lys Gly Arg Phe Thr Ile Ser Arg Asp Asn Ser Lys Asn Thr
                325                 330                 335

Leu Tyr Leu Gln Met Asn Ser Leu Arg Pro Glu Asp Thr Ala Val Tyr
            340                 345                 350

Tyr Cys Ala Lys Asp Pro Ser Pro Tyr Tyr Arg Gly Ser Ala Tyr Leu
        355                 360                 365

Leu Ser Gly Ser Tyr Asp Ser Trp Gly Gln Gly Thr Leu Val Thr Val
370                 375                 380

Ser Ser
385

<210> SEQ ID NO 10
<211> LENGTH: 386
<212> TYPE: PRT
<213> ORGANISM: Artificial Sequence
<220> FEATURE:
<223> OTHER INFORMATION: CDR sequence

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ile Phe Ser Leu Pro
            20                  25                  30

Ala Ser Gly Asn Ile Phe Asn Leu Leu Thr Ile Ala Trp Tyr Arg Gln
        35                  40                  45

Ala Pro Gly Lys Gly Arg Glu Leu Val Ala Thr Ile Asn Ser Gly Ser
50                  55                  60
```

```
Arg Thr Tyr Tyr Ala Asp Ser Val Lys Gly Arg Phe Thr Ile Ser Arg
 65                  70                  75                  80

Asp Asn Ser Lys Lys Thr Leu Tyr Leu Gln Met Asn Ser Leu Arg Pro
                 85                  90                  95

Glu Asp Thr Ala Val Tyr Tyr Cys Gln Thr Gly Ser Gly Ser Pro
            100                 105                 110

Asn Phe Trp Gly Gln Gly Thr Leu Val Thr Val Ser Ser Gly Gly Gly
            115                 120                 125

Gly Ser Gly Gly Gly Ser Glu Val Gln Leu Val Glu Ser Gly Gly Gly
        130                 135                 140

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
                165                 170                 175

Lys Gly Leu Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser Gly Gly Gly Ser Gly Gly
                245                 250                 255

Gly Ser Glu Val Gln Leu Leu Ser Gly Gly Leu Val Gln Pro
        260                 265                 270

Gly Gly Ser Leu Arg Leu Ser Cys Ala Ala Ser Gly Arg Thr Leu Ser
        275                 280                 285

Ser Tyr Ala Met Gly Trp Phe Arg Gln Ala Pro Gly Lys Gly Arg Glu
        290                 295                 300

Phe Val Ser Arg Ile Ser Gln Gly Gly Thr Ala Ile Tyr Tyr Ala Asp
305                 310                 315                 320

Ser Val Lys Gly Arg Phe Thr Ile Ser Arg Asp Asn Ser Lys Asn Thr
                325                 330                 335

Leu Tyr Leu Gln Met Asn Ser Leu Arg Pro Glu Asp Thr Ala Val Tyr
            340                 345                 350

Tyr Cys Ala Lys Asp Pro Ser Pro Tyr Tyr Arg Gly Ser Ala Tyr Leu
            355                 360                 365

Leu Ser Gly Ser Tyr Asp Ser Trp Gly Gln Gly Thr Leu Val Thr Val
        370                 375                 380

Ser Ser
385

<210> SEQ ID NO 11
<211> LENGTH: 386
<212> TYPE: PRT
<213> ORGANISM: Artificial Sequence
<220> FEATURE:
<223> OTHER INFORMATION: CDR sequence

<400> SEQUENCE: 11

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Arg Ile Phe Ser Leu Pro
             20                  25                  30
```

Ala Ser Gly Asn Ile Phe Asn Leu Leu Thr Ile Ala Trp Tyr Arg Gln
            35                  40                  45

Ala Pro Gly Lys Gly Arg Glu Leu Val Ala Thr Ile Asn Ser Gly Ser
 50                  55                  60

Arg Thr Asn Tyr Ala Asp Ser Val Lys Gly Arg Phe Thr Ile Ser Arg
 65                  70                  75                  80

Asp Asn Ser Lys Lys Thr Leu Tyr Leu Gln Met Asn Ser Leu Arg Pro
                 85                  90                  95

Glu Asp Thr Ala Val Tyr Tyr Cys Gln Thr Ser Gly Ser Gly Ser Pro
                100                 105                 110

Asn Phe Trp Gly Gln Gly Thr Leu Val Thr Val Ser Ser Gly Gly Gly
            115                 120                 125

Gly Ser Gly Gly Gly Ser Glu Val Gln Leu Val Glu Ser Gly Gly Gly
            130                 135                 140

Leu Val Gln Pro Gly Asn Ser Leu Arg Leu Ser Cys Ala Ala Ser Gly
145                 150                 155                 160

Phe Thr Phe Arg Ser Phe Gly Met Ser Trp Val Arg Gln Ala Pro Gly
                165                 170                 175

Lys Glu Pro Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
            195                 200                 205

Ala Lys Thr Thr Leu Tyr Leu Gln Met Asn Ser Leu Lys Pro Glu Asp
            210                 215                 220

Thr Ala Val Tyr Tyr Cys Thr Ile Gly Gly Ser Leu Ser Arg Ser Ser
225                 230                 235                 240

Gln Gly Thr Gln Val Thr Val Ser Ser Gly Gly Gly Ser Gly Gly Gly
                245                 250                 255

Gly Ser Glu Val Gln Leu Leu Glu Ser Gly Gly Gly Leu Val Gln Pro
            260                 265                 270

Gly Gly Ser Leu Arg Leu Ser Cys Ala Ala Ser Gly Arg Thr Leu Ser
            275                 280                 285

Ser Tyr Ala Met Gly Trp Phe Arg Gln Ala Pro Gly Lys Gly Arg Glu
            290                 295                 300

Phe Val Ser Arg Ile Ser Gln Gly Gly Thr Ala Ile Tyr Tyr Ala Asp
305                 310                 315                 320

Ser Val Lys Gly Arg Phe Thr Ile Ser Arg Asp Asn Ser Lys Asn Thr
                325                 330                 335

Leu Tyr Leu Gln Met Asn Ser Leu Arg Pro Glu Asp Thr Ala Val Tyr
            340                 345                 350

Tyr Cys Ala Lys Asp Pro Ser Pro Tyr Tyr Arg Gly Ser Ala Tyr Leu
            355                 360                 365

Leu Ser Gly Ser Tyr Asp Ser Trp Gly Gln Gly Thr Leu Val Thr Val
            370                 375                 380

Ser Ser
385

<210> SEQ ID NO 12
<211> LENGTH: 386
<212> TYPE: PRT
<213> ORGANISM: Artificial Sequence
<220> FEATURE:
<223> OTHER INFORMATION: CDR sequence

```
<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ile Phe Ser Leu Pro
            20                  25                  30

Ala Ser Gly Asn Ile Phe Asn Leu Leu Thr Ile Ala Trp Tyr Arg Gln
            35                  40                  45

Ala Pro Gly Lys Gly Arg Glu Leu Val Ala Thr Ile Asn Ser Gly Ser
    50                  55                  60

Arg Thr Tyr Tyr Ala Asp Ser Val Lys Gly Arg Phe Thr Ile Ser Arg
65                  70                  75                  80

Asp Asn Ser Lys Lys Thr Leu Tyr Leu Gln Met Asn Ser Leu Arg Pro
                85                  90                  95

Glu Asp Thr Ala Val Tyr Tyr Cys Gln Thr Ser Gly Ser Gly Ser Pro
            100                 105                 110

Asn Phe Trp Gly Gln Gly Thr Leu Val Thr Val Ser Ser Gly Gly Gly
            115                 120                 125

Gly Ser Gly Gly Gly Ser Glu Val Gln Leu Val Glu Ser Gly Gly Gly
        130                 135                 140

Leu Val Gln Pro Gly Asn Ser Leu Arg Leu Ser Cys Ala Ala Ser Gly
145                 150                 155                 160

Phe Thr Phe Arg Ser Phe Gly Met Ser Trp Val Arg Gln Ala Pro Gly
                165                 170                 175

Lys Glu Pro Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Lys Pro Glu Asp
    210                 215                 220

Thr Ala Val Tyr Tyr Cys Thr Ile Gly Gly Ser Leu Ser Arg Ser Ser
225                 230                 235                 240

Gln Gly Thr Gln Val Thr Val Ser Ser Gly Gly Gly Gly Ser Gly Gly
                245                 250                 255

Gly Ser Glu Val Gln Leu Leu Glu Ser Gly Gly Gly Leu Val Gln Pro
            260                 265                 270

Gly Gly Ser Leu Arg Leu Ser Cys Ala Ala Ser Gly Arg Thr Leu Ser
        275                 280                 285

Ser Tyr Ala Met Gly Trp Phe Arg Gln Ala Pro Gly Lys Gly Arg Glu
    290                 295                 300

Phe Val Ser Arg Ile Ser Gln Gly Gly Thr Ala Ile Tyr Tyr Ala Asp
305                 310                 315                 320

Ser Val Lys Gly Arg Phe Thr Ile Ser Arg Asp Asn Ser Lys Asn Thr
                325                 330                 335

Leu Tyr Leu Gln Met Asn Ser Leu Arg Pro Glu Asp Thr Ala Val Tyr
            340                 345                 350

Tyr Cys Ala Lys Asp Pro Ser Pro Tyr Tyr Arg Gly Ser Ala Tyr Leu
        355                 360                 365

Leu Ser Gly Ser Tyr Asp Ser Trp Gly Gln Gly Thr Leu Val Thr Val
    370                 375                 380

Ser Ser
385
```

-continued

```
<210> SEQ ID NO 13
<211> LENGTH: 386
<212> TYPE: PRT
<213> ORGANISM: Artificial Sequence
<220> FEATURE:
<223> OTHER INFORMATION: CDR sequence

<400> SEQUENCE: 13
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ile Phe Ser Leu Pro
            20                  25                  30

Ala Ser Gly Asn Ile Phe Asn Leu Leu Thr Ile Ala Trp Tyr Arg Gln
        35                  40                  45

Ala Pro Gly Lys Gly Arg Glu Leu Val Ala Thr Ile Asn Ser Gly Ser
    50                  55                  60

Arg Thr Tyr Tyr Ala Asp Ser Val Lys Gly Arg Phe Thr Ile Ser Arg
65                  70                  75                  80

Asp Asn Ser Lys Lys Thr Leu Tyr Leu Gln Met Asn Ser Leu Arg Pro
                85                  90                  95

Glu Asp Thr Ala Val Tyr Tyr Cys Gln Thr Ser Gly Ser Gly Ser Pro
            100                 105                 110

Asn Phe Trp Gly Gln Gly Thr Leu Val Thr Val Ser Ser Gly Gly Gly
        115                 120                 125

Gly Ser Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
                165                 170                 175

Lys Gly Leu Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser Gly Gly Gly Ser Gly Gly
                245                 250                 255

Gly Ser Glu Val Gln Leu Leu Glu Ser Gly Gly Gly Leu Val Gln Pro
            260                 265                 270

Gly Gly Ser Leu Arg Leu Ser Cys Ala Ala Ser Gly Arg Thr Leu Ser
        275                 280                 285

Ser Tyr Ala Met Gly Trp Phe Arg Gln Ala Pro Gly Lys Gly Arg Glu
    290                 295                 300

Phe Val Ala Arg Ile Ser Gln Gly Gly Thr Ala Ile Tyr Tyr Ala Asp
305                 310                 315                 320

Ser Val Lys Gly Arg Phe Thr Ile Ser Arg Asp Asn Ser Lys Asn Thr
                325                 330                 335

Leu Tyr Leu Gln Met Asn Ser Leu Arg Pro Glu Asp Thr Ala Val Tyr
            340                 345                 350

Tyr Cys Ala Lys Asp Pro Ser Pro Tyr Tyr Arg Gly Ser Ala Tyr Leu
        355                 360                 365

```
Leu Ser Gly Ser Tyr Asp Ser Trp Gly Gln Gly Thr Leu Val Thr Val
            370                 375                 380

Ser Ser
385

<210> SEQ ID NO 14
<211> LENGTH: 386
<212> TYPE: PRT
<213> ORGANISM: Artificial Sequence
<220> FEATURE:
<223> OTHER INFORMATION: CDR sequence

<400> SEQUENCE: 14

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ile Phe Ser Leu Pro
            20                  25                  30

Ala Ser Gly Asn Ile Phe Asn Leu Leu Thr Ile Ala Trp Tyr Arg Gln
        35                  40                  45

Ala Pro Gly Lys Gly Arg Glu Leu Val Ala Thr Ile Asn Ser Gly Ser
    50                  55                  60

Arg Thr Tyr Tyr Ala Asp Ser Val Lys Gly Arg Phe Thr Ile Ser Arg
65                  70                  75                  80

Asp Asn Ser Lys Lys Thr Val Tyr Leu Gln Met Asn Ser Leu Arg Pro
                85                  90                  95

Glu Asp Thr Ala Val Tyr Tyr Cys Gln Thr Ser Gly Ser Gly Ser Pro
            100                 105                 110

Asn Phe Trp Gly Gln Gly Thr Leu Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
                165                 170                 175

Lys Gly Leu Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser Gly Gly Gly Gly Ser Gly Gly
                245                 250                 255

Gly Ser Glu Val Gln Leu Leu Glu Ser Gly Gly Gly Leu Val Gln Pro
            260                 265                 270

Gly Gly Ser Leu Arg Leu Ser Cys Ala Ala Ser Gly Arg Thr Leu Ser
        275                 280                 285

Ser Tyr Ala Met Gly Trp Phe Arg Gln Ala Pro Gly Lys Gly Arg Glu
    290                 295                 300

Phe Val Ser Arg Ile Ser Gln Gly Gly Thr Ala Ile Tyr Tyr Ala Asp
305                 310                 315                 320

Ser Val Lys Gly Arg Phe Thr Ile Ser Arg Asp Asn Ser Lys Asn Thr
                325                 330                 335
```

```
Leu Tyr Leu Gln Met Asn Ser Leu Arg Pro Glu Asp Thr Ala Val Tyr
            340                 345                 350

Tyr Cys Ala Lys Asp Pro Ser Pro Tyr Tyr Arg Gly Ser Ala Tyr Leu
            355                 360                 365

Leu Ser Gly Ser Tyr Asp Ser Trp Gly Gln Gly Thr Leu Val Thr Val
            370                 375                 380

Ser Ser
385

<210> SEQ ID NO 15
<211> LENGTH: 386
<212> TYPE: PRT
<213> ORGANISM: Artificial Sequence
<220> FEATURE:
<223> OTHER INFORMATION: CDR sequence

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ile Phe Ser Leu Pro
            20                  25                  30

Ala Ser Gly Asn Ile Phe Asn Leu Leu Thr Ile Ala Trp Tyr Arg Gln
            35                  40                  45

Ala Pro Gly Lys Gly Arg Glu Leu Val Ala Thr Ile Asn Ser Gly Ser
        50                  55                  60

Arg Thr Tyr Tyr Ala Asp Ser Val Lys Gly Arg Phe Thr Ile Ser Arg
65                  70                  75                  80

Asp Asn Ser Lys Lys Thr Val Tyr Leu Gln Met Asn Ser Leu Arg Pro
                85                  90                  95

Glu Asp Thr Ala Val Tyr Tyr Cys Gln Thr Gly Ser Gly Ser Pro
            100                 105                 110

Asn Phe Trp Gly Gln Gly Thr Leu Val Thr Val Ser Ser Gly Gly Gly
            115                 120                 125

Gly Ser Gly Gly Gly Ser Glu Val Gln Leu Val Glu Ser Gly Gly Gly
        130                 135                 140

Leu Val Gln Pro Gly Asn Ser Leu Arg Leu Ser Cys Ala Ala Ser Gly
145                 150                 155                 160

Phe Thr Phe Arg Ser Phe Gly Met Ser Trp Val Arg Gln Ala Pro Gly
                165                 170                 175

Lys Glu Pro Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
            195                 200                 205

Ala Lys Thr Thr Leu Tyr Leu Gln Met Asn Ser Leu Lys Pro Glu Asp
        210                 215                 220

Thr Ala Val Tyr Tyr Cys Thr Ile Gly Gly Ser Leu Ser Arg Ser Ser
225                 230                 235                 240

Gln Gly Thr Gln Val Thr Val Ser Ser Gly Gly Gly Ser Gly Gly
                245                 250                 255

Gly Ser Glu Val Gln Leu Leu Glu Ser Gly Gly Gly Leu Val Gln Pro
            260                 265                 270

Gly Gly Ser Leu Arg Leu Ser Cys Ala Ala Ser Gly Arg Thr Leu Ser
            275                 280                 285

Ser Tyr Ala Met Gly Trp Phe Arg Gln Ala Pro Gly Lys Gly Arg Glu
            290                 295                 300
```

Phe Val Ser Arg Ile Ser Gln Gly Gly Thr Ala Ile Tyr Tyr Ala Asp
305                 310                 315                 320

Ser Val Lys Gly Arg Phe Thr Ile Ser Arg Asp Asn Ser Lys Asn Thr
            325                 330                 335

Leu Tyr Leu Gln Met Asn Ser Leu Arg Pro Glu Asp Thr Ala Val Tyr
        340                 345                 350

Tyr Cys Ala Lys Asp Pro Ser Pro Tyr Tyr Arg Gly Ser Ala Tyr Leu
    355                 360                 365

Leu Ser Gly Ser Tyr Asp Ser Trp Gly Gln Gly Thr Leu Val Thr Val
    370                 375                 380

Ser Ser
385

<210> SEQ ID NO 16
<211> LENGTH: 386
<212> TYPE: PRT
<213> ORGANISM: Artificial Sequence
<220> FEATURE:
<223> OTHER INFORMATION: CDR sequence

<400> SEQUENCE: 16

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ile Phe Ser Leu Pro
            20                  25                  30

Ala Ser Gly Asn Ile Phe Asn Leu Leu Thr Ile Ala Trp Tyr Arg Gln
        35                  40                  45

Ala Pro Gly Lys Gly Arg Glu Leu Val Ala Thr Ile Asn Ser Gly Ser
    50                  55                  60

Arg Thr Tyr Tyr Ala Asp Ser Val Lys Gly Arg Phe Thr Ile Ser Arg
65                  70                  75                  80

Asp Asn Ser Lys Lys Thr Val Tyr Leu Gln Met Asn Ser Leu Arg Pro
            85                  90                  95

Glu Asp Thr Ala Val Tyr Tyr Cys Gln Thr Gly Ser Gly Ser Pro
            100                 105                 110

Asn Phe Trp Gly Gln Gly Thr Leu Val Thr Val Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
            165                 170                 175

Lys Gly Leu Glu Trp Val Ser Ser Ile Ser Gly Ser Gly Ser Asp Thr
        180                 185                 190

Leu Tyr Ala Asp Ser Val Lys Gly Arg Phe Thr Ile Ser Arg Asp Asn
    195                 200                 205

Ala Lys Thr Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser Gly Gly Gly Ser Gly Gly
            245                 250                 255

Gly Ser Glu Val Gln Leu Leu Glu Ser Gly Gly Gly Leu Val Gln Pro
        260                 265                 270

Gly Gly Ser Leu Arg Leu Ser Cys Ala Ala Ser Gly Arg Thr Leu Ser
            275                 280                 285

Ser Tyr Ala Met Gly Trp Phe Arg Gln Ala Pro Gly Lys Gly Arg Glu
290                 295                 300

Phe Val Ala Arg Ile Ser Gln Gly Gly Thr Ala Ile Tyr Tyr Ala Asp
305                 310                 315                 320

Ser Val Lys Gly Arg Phe Thr Ile Ser Arg Asp Asn Ser Lys Asn Thr
                325                 330                 335

Leu Tyr Leu Gln Met Asn Ser Leu Arg Pro Glu Asp Thr Ala Val Tyr
            340                 345                 350

Tyr Cys Ala Lys Asp Pro Ser Pro Tyr Tyr Arg Gly Ser Ala Tyr Leu
        355                 360                 365

Leu Ser Gly Ser Tyr Asp Ser Trp Gly Gln Gly Thr Leu Val Thr Val
    370                 375                 380

Ser Ser
385

<210> SEQ ID NO 17
<211> LENGTH: 386
<212> TYPE: PRT
<213> ORGANISM: Artificial Sequence
<220> FEATURE:
<223> OTHER INFORMATION: CDR sequence

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ile Phe Ser Leu Pro
            20                  25                  30

Ala Ser Gly Asn Ile Phe Asn Leu Leu Thr Ile Ala Trp Tyr Arg Gln
        35                  40                  45

Ala Pro Gly Lys Gly Arg Glu Leu Val Ala Thr Ile Asn Ser Gly Ser
    50                  55                  60

Arg Thr Tyr Tyr Ala Asp Ser Val Lys Gly Arg Phe Thr Ile Ser Arg
65                  70                  75                  80

Asp Asn Ser Lys Lys Thr Val Tyr Leu Gln Met Asn Ser Leu Arg Pro
                85                  90                  95

Glu Asp Thr Ala Val Tyr Tyr Cys Gln Thr Ser Gly Ser Gly Ser Pro
            100                 105                 110

Asn Phe Trp Gly Gln Gly Thr Leu Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Arg Ser Phe Gly Met Ser Trp Val Arg Gln Ala Pro Gly
                165                 170                 175

Lys Glu Pro Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Lys Pro Glu Asp
    210                 215                 220

Thr Ala Val Tyr Tyr Cys Thr Ile Gly Gly Ser Leu Ser Arg Ser Ser
225                 230                 235                 240

```
Gln Gly Thr Gln Val Thr Val Ser Ser Gly Gly Gly Ser Gly Gly
                    245                 250                 255
Gly Ser Glu Val Gln Leu Val Glu Ser Gly Gly Leu Val Gln Ala
            260                 265                 270
Gly Gly Ser Leu Arg Leu Ser Cys Ala Ala Ser Gly Arg Thr Leu Ser
        275                 280                 285
Ser Tyr Ala Met Gly Trp Phe Arg Gln Ala Pro Gly Lys Glu Arg Glu
    290                 295                 300
Phe Val Ala Arg Ile Ser Gln Gly Gly Thr Ala Ile Tyr Tyr Ala Asp
305                 310                 315                 320
Ser Val Lys Gly Arg Phe Thr Ile Ser Arg Asp Asn Ala Lys Asn Thr
                325                 330                 335
Val Tyr Leu Gln Met Asn Ser Leu Lys Pro Glu Asp Thr Ala Val Tyr
            340                 345                 350
Tyr Cys Ala Lys Asp Pro Ser Pro Tyr Tyr Arg Gly Ser Ala Tyr Leu
        355                 360                 365
Leu Ser Gly Ser Tyr Asp Ser Trp Gly Gln Gly Thr Gln Val Thr Val
    370                 375                 380
Ser Ser
385

<210> SEQ ID NO 18
<211> LENGTH: 386
<212> TYPE: PRT
<213> ORGANISM: Artificial Sequence
<220> FEATURE:
<223> OTHER INFORMATION: CDR sequence

<400> SEQUENCE: 18

Glu Val Gln Leu Leu Glu Ser Gly Gly Gly Leu Val Gln Pro Gly Gly
1               5                   10                  15
Ser Leu Arg Leu Ser Cys Ala Ala Ser Gly Arg Ile Phe Ser Leu Pro
            20                  25                  30
Ala Ser Gly Asn Ile Phe Asn Leu Leu Thr Ile Ala Trp Tyr Arg Gln
        35                  40                  45
Ala Pro Gly Lys Gly Arg Glu Leu Val Ala Thr Ile Asn Ser Gly Ser
    50                  55                  60
Arg Thr Tyr Tyr Ala Asp Ser Val Lys Gly Arg Phe Thr Ile Ser Arg
65                  70                  75                  80
Asp Asn Ser Lys Lys Thr Val Tyr Leu Gln Met Asn Ser Leu Arg Pro
                85                  90                  95
Glu Asp Thr Ala Val Tyr Tyr Cys Gln Thr Ser Gly Ser Gly Ser Pro
            100                 105                 110
Asn Phe Trp Gly Gln Gly Thr Leu Val Thr Val Ser Gly Gly Gly
        115                 120                 125
Gly Ser Gly Gly Gly Ser Glu Val Gln Leu Val Glu Ser Gly Gly Gly
    130                 135                 140
Leu Val Gln Pro Gly Asn Ser Leu Arg Leu Ser Cys Ala Ala Ser Gly
145                 150                 155                 160
Phe Thr Phe Ser Ser Phe Gly Met Ser Trp Val Arg Gln Ala Pro Gly
                165                 170                 175
Lys Gly Leu Glu Trp Val Ser Ser Ile Ser Gly Ser Gly Ser Asp Thr
            180                 185                 190
Leu Tyr Ala Asp Ser Val Lys Gly Arg Phe Thr Ile Ser Arg Asp Asn
        195                 200                 205
```

Ala Lys Thr Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser Gly Gly Gly Ser Gly Gly
                245                 250                 255

Gly Ser Glu Val Gln Leu Leu Glu Ser Gly Gly Gly Leu Val Gln Pro
            260                 265                 270

Gly Gly Ser Leu Arg Leu Ser Cys Ala Ala Ser Gly Arg Thr Leu Ser
        275                 280                 285

Ser Tyr Ala Met Gly Trp Phe Arg Gln Ala Pro Gly Lys Gly Arg Glu
    290                 295                 300

Phe Val Ala Arg Ile Ser Gln Gly Gly Thr Ala Ile Tyr Tyr Ala Asp
305                 310                 315                 320

Ser Val Lys Gly Arg Phe Thr Ile Ser Arg Asp Asn Ser Lys Asn Thr
                325                 330                 335

Leu Tyr Leu Gln Met Asn Ser Leu Arg Pro Glu Asp Thr Ala Val Tyr
            340                 345                 350

Tyr Cys Ala Lys Asp Pro Ser Pro Tyr Tyr Arg Gly Ser Ala Tyr Leu
        355                 360                 365

Leu Ser Gly Ser Tyr Asp Ser Trp Gly Gln Gly Thr Leu Val Thr Val
    370                 375                 380

Ser Ser
385

<210> SEQ ID NO 19
<211> LENGTH: 386
<212> TYPE: PRT
<213> ORGANISM: Artificial Sequence
<220> FEATURE:
<223> OTHER INFORMATION: CDR sequence

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ile Phe Ser Leu Pro
            20                  25                  30

Ala Ser Gly Asn Ile Phe Asn Leu Leu Thr Ile Ala Trp Tyr Arg Gln
        35                  40                  45

Ala Pro Gly Lys Gly Arg Glu Leu Val Ala Thr Ile Asn Ser Gly Ser
    50                  55                  60

Arg Thr Tyr Tyr Ala Asp Ser Val Lys Gly Arg Phe Thr Ile Ser Arg
65                  70                  75                  80

Asp Asn Ser Lys Lys Thr Val Tyr Leu Gln Met Asn Ser Leu Arg Pro
                85                  90                  95

Glu Asp Thr Ala Val Tyr Tyr Cys Gln Thr Ser Gly Ser Gly Ser Pro
            100                 105                 110

Asn Phe Trp Gly Gln Gly Thr Leu Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
                165                 170                 175

```
Lys Gly Leu Glu Trp Val Ser Ser Ile Ser Gly Ser Gly Ser Asp Thr
            180                 185                 190
Leu Tyr Ala Asp Ser Val Lys Gly Arg Phe Thr Ile Ser Arg Asp Asn
        195                 200                 205
Ala Lys Thr Thr Leu Tyr Leu Gln Met Asn Ser Leu Arg Pro Glu Asp
    210                 215                 220
Thr Ala Val Tyr Tyr Cys Thr Ile Gly Gly Ser Leu Ser Arg Ser Ser
225                 230                 235                 240
Gln Gly Thr Leu Val Thr Val Ser Ser Gly Gly Gly Ser Gly Gly
            245                 250                 255
Gly Ser Glu Val Gln Leu Leu Glu Ser Gly Gly Gly Leu Val Gln Pro
        260                 265                 270
Gly Gly Ser Leu Arg Leu Ser Cys Ala Ala Ser Gly Arg Thr Leu Ser
    275                 280                 285
Ser Tyr Ala Met Gly Trp Phe Arg Gln Ala Pro Gly Lys Gly Arg Glu
290                 295                 300
Phe Val Ala Arg Ile Ser Gln Gly Gly Thr Ala Ile Tyr Tyr Ala Asp
305                 310                 315                 320
Ser Val Lys Gly Arg Phe Thr Ile Ser Arg Asp Asn Ser Lys Asn Thr
            325                 330                 335
Val Tyr Leu Gln Met Asn Ser Leu Arg Pro Glu Asp Thr Ala Val Tyr
        340                 345                 350
Tyr Cys Ala Lys Asp Pro Ser Tyr Tyr Arg Gly Ser Ala Tyr Leu
    355                 360                 365
Leu Ser Gly Ser Tyr Asp Ser Trp Gly Gln Gly Thr Leu Val Thr Val
    370                 375                 380
Ser Ser
385

<210> SEQ ID NO 20
<211> LENGTH: 386
<212> TYPE: PRT
<213> ORGANISM: Artificial Sequence
<220> FEATURE:
<223> OTHER INFORMATION: CDR sequence

<400> SEQUENCE: 20

Glu Val Gln Leu Leu Glu Ser Gly Gly Gly Leu Val Gln Pro Gly Gly
1               5                   10                  15
Ser Leu Arg Leu Ser Cys Ala Ala Ser Gly Arg Ile Phe Ser Leu Pro
            20                  25                  30
Ala Ser Gly Asn Ile Phe Asn Leu Leu Thr Ile Ala Trp Tyr Arg Gln
        35                  40                  45
Ala Pro Gly Lys Gly Arg Glu Leu Val Ala Thr Ile Asn Ser Gly Ser
    50                  55                  60
Arg Thr Tyr Tyr Ala Asp Ser Val Lys Gly Arg Phe Thr Ile Ser Arg
65                  70                  75                  80
Asp Asn Ser Lys Lys Thr Val Tyr Leu Gln Met Asn Ser Leu Arg Pro
                85                  90                  95
Glu Asp Thr Ala Val Tyr Tyr Cys Gln Thr Ser Gly Gly Ser Pro
            100                 105                 110
Asn Phe Trp Gly Gln Gly Thr Leu Val Thr Val Ser Ser Gly Gly Gly
        115                 120                 125
Gly Ser Gly Gly Gly Ser Glu Val Gln Leu Val Glu Ser Gly Gly Gly
    130                 135                 140
```

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
            165                 170                 175

Lys Gly Leu Glu Trp Val Ser Ser Ile Ser Gly Ser Gly Ser Asp Thr
        180                 185                 190

Leu Tyr Ala Asp Ser Val Lys Gly Arg Phe Thr Ile Ser Arg Asp Asn
    195                 200                 205

Ala Lys Thr Thr Leu Tyr Leu Gln Met Asn Ser Leu Arg Pro Glu Asp
210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser Gly Gly Gly Ser Gly Gly
            245                 250                 255

Gly Ser Glu Val Gln Leu Leu Glu Ser Gly Gly Gly Leu Val Gln Pro
        260                 265                 270

Gly Gly Ser Leu Arg Leu Ser Cys Ala Ala Ser Gly Arg Thr Leu Ser
        275                 280                 285

Ser Tyr Ala Met Gly Trp Phe Arg Gln Ala Pro Gly Lys Gly Arg Glu
    290                 295                 300

Phe Val Ser Arg Ile Ser Gln Gly Gly Thr Ala Ile Tyr Tyr Ala Asp
305                 310                 315                 320

Ser Val Lys Gly Arg Phe Thr Ile Ser Arg Asp Asn Ser Lys Asn Thr
                325                 330                 335

Leu Tyr Leu Gln Met Asn Ser Leu Arg Pro Glu Asp Thr Ala Val Tyr
            340                 345                 350

Tyr Cys Ala Lys Asp Pro Ser Pro Tyr Tyr Arg Gly Ser Ala Tyr Leu
        355                 360                 365

Leu Ser Gly Ser Tyr Asp Ser Trp Gly Gln Gly Thr Leu Val Thr Val
    370                 375                 380

Ser Ser
385

<210> SEQ ID NO 21
<211> LENGTH: 386
<212> TYPE: PRT
<213> ORGANISM: Artificial Sequence
<220> FEATURE:
<223> OTHER INFORMATION: CDR sequence

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ile Phe Ser Leu Pro
            20                  25                  30

Ala Ser Gly Asn Ile Phe Asn Leu Leu Thr Ile Ala Trp Tyr Arg Gln
        35                  40                  45

Ala Pro Gly Lys Gly Arg Glu Leu Val Ala Thr Ile Asn Ser Gly Ser
    50                  55                  60

Arg Thr Tyr Tyr Ala Asp Ser Val Lys Gly Arg Phe Thr Ile Ser Arg
65                  70                  75                  80

Asp Asn Ser Lys Lys Thr Val Tyr Leu Gln Met Asn Ser Leu Arg Pro
                85                  90                  95

Glu Asp Thr Ala Val Tyr Tyr Cys Gln Thr Ser Gly Ser Gly Ser Pro
            100                 105                 110

```
Asn Phe Trp Gly Gln Gly Thr Leu Val Thr Val Ser Gly Gly Gly
            115                 120                 125

Gly Ser Gly Gly Gly Ser Glu Val Gln Leu Val Glu Ser Gly Gly
        130                 135                 140

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
                165                 170                 175

Lys Gly Leu Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser Gly Gly Gly Ser Gly Gly
                245                 250                 255

Gly Ser Glu Val Gln Leu Leu Glu Ser Gly Gly Gly Leu Val Gln Pro
        260                 265                 270

Gly Gly Ser Leu Arg Leu Ser Cys Ala Ala Ser Gly Arg Thr Leu Ser
    275                 280                 285

Ser Tyr Ala Met Gly Trp Phe Arg Gln Ala Pro Gly Lys Gly Arg Glu
        290                 295                 300

Phe Val Ala Arg Ile Ser Gln Gly Gly Thr Ala Ile Tyr Tyr Ala Asp
305                 310                 315                 320

Ser Val Lys Gly Arg Phe Thr Ile Ser Arg Asp Asn Ser Lys Asn Thr
                325                 330                 335

Leu Tyr Leu Gln Met Asn Ser Leu Arg Pro Glu Asp Thr Ala Val Tyr
            340                 345                 350

Tyr Cys Ala Lys Asp Pro Ser Pro Tyr Arg Gly Ser Ala Tyr Leu
        355                 360                 365

Leu Ser Gly Ser Tyr Asp Ser Trp Gly Gln Gly Thr Leu Val Thr Val
    370                 375                 380

Ser Ser
385

<210> SEQ ID NO 22
<211> LENGTH: 386
<212> TYPE: PRT
<213> ORGANISM: Artificial Sequence
<220> FEATURE:
<223> OTHER INFORMATION: CDR sequence

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ile Phe Ser Leu Pro
            20                  25                  30

Ala Ser Gly Asn Ile Phe Asn Leu Leu Thr Ile Ala Trp Tyr Arg Gln
        35                  40                  45

Ala Pro Gly Lys Gly Arg Glu Leu Val Ala Thr Ile Asn Ser Gly Ser
    50                  55                  60

Arg Thr Tyr Tyr Ala Asp Ser Val Lys Gly Arg Phe Thr Ile Ser Arg
65                  70                  75                  80
```

```
Asp Asn Ser Lys Lys Thr Val Tyr Leu Gln Met Asn Ser Leu Arg Pro
                85                  90                  95

Glu Asp Thr Ala Val Tyr Tyr Cys Gln Thr Gly Ser Gly Ser Pro
            100                 105                 110

Asn Phe Trp Gly Gln Gly Thr Leu Val Thr Val Ser Ser Gly Gly Gly
        115                 120                 125

Gly Ser Gly Gly Gly Ser Glu Val Gln Leu Val Glu Ser Gly Gly Gly
        130                 135                 140

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
                165                 170                 175

Lys Gly Leu Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser Gly Gly Gly Ser Gly Gly
                245                 250                 255

Gly Ser Glu Val Gln Leu Leu Glu Ser Gly Gly Gly Leu Val Gln Pro
            260                 265                 270

Gly Gly Ser Leu Arg Leu Ser Cys Ala Ala Ser Gly Arg Thr Leu Ser
        275                 280                 285

Ser Tyr Ala Met Gly Trp Phe Arg Gln Ala Pro Gly Lys Gly Arg Glu
    290                 295                 300

Phe Val Ala Arg Ile Ser Gln Gly Gly Thr Ala Ile Tyr Tyr Ala Asp
305                 310                 315                 320

Ser Val Lys Gly Arg Phe Thr Ile Ser Arg Asp Asn Ser Lys Asn Thr
                325                 330                 335

Leu Tyr Leu Gln Met Asn Ser Leu Arg Pro Glu Asp Thr Ala Val Tyr
            340                 345                 350

Tyr Cys Ala Lys Asp Pro Ser Pro Tyr Tyr Arg Gly Ser Ala Tyr Leu
        355                 360                 365

Leu Ser Gly Ser Tyr Asp Ser Trp Gly Gln Gly Thr Leu Val Thr Val
    370                 375                 380

Ser Ser
385

<210> SEQ ID NO 23
<211> LENGTH: 386
<212> TYPE: PRT
<213> ORGANISM: Artificial Sequence
<220> FEATURE:
<223> OTHER INFORMATION: CDR sequence

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ile Phe Ser Leu Pro
            20                  25                  30

Ala Ser Gly Asn Ile Phe Asn Leu Leu Thr Ile Ala Trp Tyr Arg Gln
        35                  40                  45
```

-continued

```
Ala Pro Gly Lys Gly Arg Glu Leu Val Ala Thr Ile Asn Ser Gly Ser
    50              55                  60
Arg Thr Tyr Tyr Ala Asp Ser Val Lys Gly Arg Phe Thr Ile Ser Arg
 65              70                  75                  80
Asp Asn Ser Lys Lys Thr Val Tyr Leu Gln Met Asn Ser Leu Arg Pro
            85                  90                  95
Glu Asp Thr Ala Val Tyr Tyr Cys Gln Thr Ser Gly Ser Gly Ser Pro
             100             105             110
Asn Phe Trp Gly Gln Gly Thr Leu Val Thr Val Ser Ser Gly Gly Gly
         115             120             125
Gly Ser Gly Gly Gly Ser Glu Val Gln Leu Val Glu Ser Gly Gly Gly
    130             135             140
Leu Val Gln Pro Gly Asn Ser Leu Arg Leu Ser Cys Ala Ala Ser Gly
145             150             155             160
Phe Thr Phe Ser Ser Phe Gly Met Ser Trp Val Arg Gln Ala Pro Gly
                165             170             175
Lys Gly Leu Glu Trp Val Ser Ser Ile Ser Gly Ser Gly Ser Asp Thr
            180             185             190
Leu Tyr Ala Asp Ser Val Lys Gly Arg Phe Thr Ile Ser Arg Asp Asn
        195             200             205
Ala Lys Thr Thr Leu Tyr Leu Gln Met Asn Ser Leu Arg Pro Glu Asp
    210             215             220
Thr Ala Val Tyr Tyr Cys Thr Ile Gly Gly Ser Leu Ser Arg Ser Ser
225             230             235             240
Gln Gly Thr Leu Val Thr Val Ser Ser Gly Gly Gly Gly Ser Gly Gly
                245             250             255
Gly Ser Glu Val Gln Leu Leu Glu Ser Gly Gly Gly Leu Val Gln Pro
            260             265             270
Gly Gly Ser Leu Arg Leu Ser Cys Ala Ala Ser Gly Arg Thr Leu Ser
        275             280             285
Ser Tyr Ala Met Gly Trp Phe Arg Gln Ala Pro Gly Lys Gly Arg Glu
    290             295             300
Phe Val Ala Arg Ile Ser Gln Gly Gly Thr Ala Ile Tyr Tyr Ala Asp
305             310             315             320
Ser Val Lys Gly Arg Phe Thr Ile Ser Arg Asp Asn Ser Lys Asn Thr
                325             330             335
Val Tyr Leu Gln Met Asn Ser Leu Arg Pro Glu Asp Thr Ala Val Tyr
            340             345             350
Tyr Cys Ala Lys Asp Pro Ser Pro Tyr Tyr Arg Gly Ser Ala Tyr Leu
        355             360             365
Leu Ser Gly Ser Tyr Asp Ser Trp Gly Gln Gly Thr Leu Val Thr Val
    370             375             380
Ser Ser
385
```